US008754028B2

(12) United States Patent
Velazquez et al.

(10) Patent No.: US 8,754,028 B2
(45) Date of Patent: Jun. 17, 2014

(54) PERFUME SYSTEMS

(75) Inventors: Jose Maria Velazquez, Ascot (GB); Rafael Trujillo Rosaldo, Mason, OH (US); Philip John Porter, Mason, OH (US); Zerlina Guzdar Dubois, Mason, OH (US); Yoshimi Sunohara, Kobe (JP); Javier Medina, Newcastle Upon Tyne (GB); Michael Green, Newcastle Upon Tyne (GB); Hugo Robert Germain Denutte, Hofstade (BE); Jonathan Richard Clare, Newcastle Upon Tyne (GB); Stacy Renee Hertenstein, Glendale, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 998 days.

(21) Appl. No.: 12/336,080

(22) Filed: Dec. 16, 2008

(65) Prior Publication Data

US 2010/0152083 A1 Jun. 17, 2010

(51) Int. Cl.

| | |
|---|---|
| ***A61K 8/00*** | (2006.01) |
| ***A61K 8/18*** | (2006.01) |
| ***A61Q 13/00*** | (2006.01) |
| ***C11D 3/02*** | (2006.01) |
| ***C11D 3/20*** | (2006.01) |
| ***C11D 3/39*** | (2006.01) |
| ***C11D 3/50*** | (2006.01) |

(52) U.S. Cl.
CPC .................................... *C11D 3/50* (2013.01)
USPC ................ 512/1; 510/108; 510/109; 510/220

(58) Field of Classification Search
USPC ............................... 510/108, 109, 220; 512/1
See application file for complete search history.

(56) References Cited

U.S. PATENT DOCUMENTS

| | | | |
|---|---|---|---|
| 3,507,761 | A | 4/1970 | Kropp |
| 3,594,324 | A | 7/1971 | Thomas et al. |
| 3,812,011 | A | 5/1974 | Okada et al. |
| 4,234,627 | A | 11/1980 | Schilling |
| 4,317,881 | A | 3/1982 | Yagi et al. |
| 4,378,923 | A | 4/1983 | Takei |
| 4,418,144 | A | 11/1983 | Okada et al. |
| 4,430,243 | A | 2/1984 | Bragg |
| 4,514,461 | A | 4/1985 | Woo |
| 4,539,135 | A | 9/1985 | Ramachandran et al. |
| 4,540,721 | A | 9/1985 | Staller |
| 4,613,680 | A | 9/1986 | Naruto et al. |
| 4,622,221 | A | 11/1986 | Schleppnik |
| 4,659,509 | A | 4/1987 | Asakawa |
| 4,709,707 | A | 12/1987 | Pittet et al. |
| 4,719,105 | A | 1/1988 | Schleppnik |
| RE32,713 | E | 7/1988 | Woo |
| 4,861,514 | A | 8/1989 | Hutchings |
| 4,882,220 | A | 11/1989 | Ono et al. |
| 4,885,274 | A | 12/1989 | Yamada et al. |
| 4,911,852 | A | 3/1990 | Coffindaffer et al. |
| 4,917,920 | A | 4/1990 | Ono et al. |
| 4,948,781 | A | 8/1990 | Kaiser et al. |
| 4,973,422 | A | 11/1990 | Schmidt |
| 5,236,615 | A | 8/1993 | Trinh et al. |
| 5,374,614 | A | 12/1994 | Behan et al. |
| 5,506,201 | A | 4/1996 | McDermott et al. |
| 5,552,378 | A | 9/1996 | Trinh et al. |
| 5,574,179 | A | 11/1996 | Wahl et al. |
| 5,576,282 | A | 11/1996 | Miracle et al. |
| 5,595,967 | A | 1/1997 | Miracle et al. |
| 5,597,936 | A | 1/1997 | Perkins et al. |
| 5,651,976 | A | 7/1997 | Price et al. |
| 5,858,959 | A | 1/1999 | Surutzidis et al. |
| 5,958,870 | A | 9/1999 | Declercq et al. |
| 6,024,943 | A | 2/2000 | Ness et al. |
| 6,042,792 | A | 3/2000 | Shefer et al. |
| 6,048,830 | A | 4/2000 | Gallon et al. |
| 6,051,540 | A | 4/2000 | Shefer et al. |
| 6,093,691 | A | 7/2000 | Sivik et al. |
| 6,096,918 | A | 8/2000 | Anderson et al. |
| 6,103,678 | A | 8/2000 | Masschelein et al. |
| 6,106,875 | A | 8/2000 | Soper et al. |
| 6,133,228 | A | 10/2000 | Pika et al. |
| 6,147,037 | A | 11/2000 | Gardlik et al. |
| 6,165,953 | A | 12/2000 | Gardlik et al. |
| 6,200,949 | B1 | 3/2001 | Reijmer et al. |

(Continued)

FOREIGN PATENT DOCUMENTS

| | | | |
|---|---|---|---|
| GB | 2048253 A | * 12/1980 | .............. C07C 47/21 |
| JP | 2002-327193 A | 11/2002 | |

(Continued)

OTHER PUBLICATIONS

Situs Oxford English Dictionary {http://dictionary.oed.com/cgi/entry/50225876?single=1&query_type=word&queryword=situs&first=1&max_to_show=10}.*

(Continued)

*Primary Examiner* — Patrick Ryan
*Assistant Examiner* — Aaron Greso
(74) *Attorney, Agent, or Firm* — James F. McBride; Steven W. Miller

(57) ABSTRACT

The present application relates to perfume raw materials, perfume systems and consumer products comprising such perfume raw materials and/or such perfume systems, as well as processes for making and using such, perfume systems and consumer products. The perfume compositions, including the delivery systems, disclosed herein expand the perfume communities' options as such perfume raw materials can provide variations on character and such compositions can provide desired odor profiles.

8 Claims, No Drawings

(56) References Cited

U.S. PATENT DOCUMENTS

| | | | |
|---|---|---|---|
| 6,218,355 | B1 | 4/2001 | Herrmann |
| 6,225,464 | B1 | 5/2001 | Hiler, II et al. |
| 6,245,732 | B1 | 6/2001 | Gallon et al. |
| 6,277,796 | B1 | 8/2001 | Sivik et al. |
| 6,306,812 | B1 | 10/2001 | Perkins et al. |
| 6,316,397 | B1 | 11/2001 | Sivik |
| 6,326,348 | B1 | 12/2001 | Vinson et al. |
| 6,413,920 | B1 | 7/2002 | Bettiol et al. |
| 6,437,150 | B1 | 8/2002 | Anderson et al. |
| 6,458,754 | B1 | 10/2002 | Velazquez et al. |
| 6,479,682 | B1 | 11/2002 | Anderson et al. |
| 6,531,444 | B1 | 3/2003 | Shefer et al. |
| 6,544,945 | B1 | 4/2003 | Miracle et al. |
| 6,610,646 | B2 | 8/2003 | Miracle et al. |
| 6,645,479 | B1 | 11/2003 | Shefer et al. |
| 6,861,402 | B1 | 3/2005 | Miracle et al. |
| 6,956,013 | B2 | 10/2005 | Dykstra et al. |
| 6,987,084 | B2 | 1/2006 | Dykstra et al. |
| 7,018,978 | B2 | 3/2006 | Miracle et al. |
| 7,071,151 | B2 | 7/2006 | Dykstra et al. |
| 7,109,153 | B2 | 9/2006 | Dykstra et al. |
| 7,119,060 | B2 | 10/2006 | Shefer et al. |
| 2003/0036489 | A1 | 2/2003 | Liu et al. |
| 2003/0125222 | A1 | 7/2003 | Jahns et al. |
| 2003/0134772 | A1 | 7/2003 | Dykstra et al. |
| 2003/0158344 | A1 | 8/2003 | Rodriques et al. |
| 2003/0165692 | A1 | 9/2003 | Koch et al. |
| 2003/0195133 | A1 | 10/2003 | Shefer et al. |
| 2003/0199422 | A1 | 10/2003 | Birkbeck et al. |
| 2003/0203829 | A1 | 10/2003 | Shefer et al. |
| 2003/0215417 | A1 | 11/2003 | Uchiyama et al. |
| 2003/0216488 | A1 | 11/2003 | Uchiyama et al. |
| 2004/0058845 | A1 | 3/2004 | Metrot et al. |
| 2004/0071742 | A1 | 4/2004 | Popplewell et al. |
| 2004/0071746 | A1 | 4/2004 | Popplewell et al. |
| 2004/0072719 | A1 | 4/2004 | Bennett et al. |
| 2004/0072720 | A1 | 4/2004 | Brain et al. |
| 2004/0087476 | A1 | 5/2004 | Dykstra et al. |
| 2004/0087477 | A1 | 5/2004 | Ness |
| 2004/0091445 | A1 | 5/2004 | Dykstra et al. |
| 2004/0092414 | A1 | 5/2004 | Clapp et al. |
| 2004/0092425 | A1 | 5/2004 | Boutique et al. |
| 2004/0106536 | A1 | 6/2004 | Mane et al. |
| 2004/0110648 | A1 | 6/2004 | Jordan, IV et al. |
| 2004/0220074 | A1 | 11/2004 | Fehr et al. |
| 2005/0003980 | A1 | 1/2005 | Baker et al. |
| 2005/0124530 | A1 | 6/2005 | Creutz |
| 2005/0143282 | A1 | 6/2005 | Creutz |
| 2006/0003913 | A1 | 1/2006 | Boutique et al. |
| 2006/0020459 | A1 | 1/2006 | Carter et al. |
| 2006/0039934 | A1 | 2/2006 | Ness et al. |
| 2006/0223726 | A1 | 10/2006 | Dykstra et al. |
| 2006/0263313 | A1 | 11/2006 | Scavone et al. |
| 2007/0275866 | A1 | 11/2007 | Dykstra |
| 2008/0200363 | A1 * | 8/2008 | Smets et al. .................. 510/475 |
| 2008/0305977 | A1 | 12/2008 | Smets et al. |

FOREIGN PATENT DOCUMENTS

| | | | | |
|---|---|---|---|---|
| JP | 2007-070269 | A | 3/2007 | |
| JP | 2008-156516 | A | 7/2008 | |
| JP | 2008-297355 | A | 12/2008 | |
| WO | WO 00/32601 | A2 | 6/2000 | |
| WO | WO 03/015736 | A2 | 2/2003 | |
| WO | WO03070871 | A1 * | 8/2003 | ............... C11D 3/50 |
| WO | WO 2005/102261 | A1 | 11/2005 | |
| WO | WO 2006/053615 | A1 | 5/2006 | |

OTHER PUBLICATIONS

Mugeut Oxford English Dictionary {http://dictionary.oed.com/cgi/entry/00317754?single=1 &query_type=word&queryword=muguet&first=1&max_to_show=10}.*

Leffingwell (Miscellaneous Odorants by John C. Leffingwell, Ph.D.; {http://www.leffingwell.com/chirality/miscellaneous.htm} (see corresponding entries on p. 2 and 14 of Leffingwell), online Feb. 2003 © 2002 Leffingwell and Associates.*

International Search Report, International Application No. PCT/IB2008/055474, Mailed Aug. 6, 2009, 6 pages.

* cited by examiner

PERFUME SYSTEMS

FIELD OF INVENTION

The present application relates to perfume raw materials, perfume delivery systems and consumer products comprising such perfume raw materials and/or such perfume delivery systems, as well as processes for making and using such perfume raw materials, perfume delivery systems and consumer products.

BACKGROUND OF THE INVENTION

Consumer products may comprise one or more perfumes and/or perfume delivery systems that can provide a desired scent to such product and/or a situs that is contacted with such a product and/or mask an undesirable odor. While current perfumes and perfume delivery systems provide desirable odors, consumers continue to seek products that have scents that may be longer lasting and that are tailored to their individual desires (see for example USPA 2007/0275866 A1 and U.S. patent application Ser. No. 12/133,866)—unfortunately the pool of perfume raw materials and perfume delivery systems that is available is still too limited, due for example to potential supply constraints, to completely meet the perfume community's needs. Thus, perfumers need an ever larger pool of perfume raw materials and perfume delivery systems that can replace current or serve as alternatives to current perfume materials.

Applicants believe that the perfume raw materials and compositions, including the delivery systems, disclosed herein expand the perfume community's options, as such perfume raw materials can provide the overall performance, including, for example, character and/or odor profiles, of p-tert.Butyl-alpha-methyldihydrocinnamic aldehyde which is also known as Lilial®.

SUMMARY OF THE INVENTION

The present application relates to perfume raw materials, perfume systems and consumer products comprising such perfume raw materials and/or such perfume systems, as well as processes for making and using such, perfume systems and consumer products.

DETAILED DESCRIPTION OF THE INVENTION

Definitions

As used herein "consumer product" means baby care, beauty care, fabric & home care, family care, feminine care, health care, snack and/or beverage products or devices generally intended to be used or consumed in the form in which it is sold. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for and/or methods relating to treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee.

As used herein, the term "cleaning and/or treatment composition" is a subset of consumer products that includes, unless otherwise indicated, beauty care, fabric & home care products. Such products include, but are not limited to, products for treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners including toilet bowl cleaners; hair shampoos and hair-rinses; shower gels, fine fragrances and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists all for consumer or/and institutional use; and/or methods relating to oral care including toothpastes, tooth gels, tooth rinses, denture adhesives, tooth whitening.

As used herein, the term "fabric and/or hard surface cleaning and/or treatment composition" is a subset of cleaning and treatment compositions that includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, car or carpet shampoos, bathroom cleaners including toilet bowl cleaners; and metal cleaners, fabric conditioning products including softening and/or freshening that may be in liquid, solid and/or dryer sheet form; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists. All of such products which were applicable may be in standard, concentrated or even highly concentrated form even to the extent that such products may in certain aspect be non-aqueous.

As used herein, articles such as "a" and "an" when used in a claim, are understood to mean one or more of what is claimed or described.

As used herein, the terms "include", "includes" and "including" are meant to be non-limiting.

As used herein, the term "solid" includes granular, powder, bar and tablet product forms.

As used herein, the term "fluid" includes liquid, gel, paste and gas product forms.

As used herein, the term "situs" includes paper products, fabrics, garments, hard surfaces, hair and skin.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Suitable Perfume Raw Materials (Herein after "PRMs")

Suitable PRMs for forming a p-tert.Butyl-alpha-methyldihydrocinnamic aldehyde (CAS No. 80-54-6) replacement include the PRMs listed in Table 1 below, and stereoisomers of such PRMs.

TABLE 1 p-tert.Butyl-alpha-methyldihydrocinnamic aldehyde replacement materials (PRMs)

| Ingredient | CAS NUMBER | Chemical name | Trade Name | Chemical Type |
|---|---|---|---|---|
| 1 | 2050-08-0 | n-Pentyl salicylate | Amyl Salicylate | Ester |
| 2 | 89-43-0 | Methyl-N-(7-hydroxy-3,7-dimethyloctylidene)anthranilate | Aurantiol ® Pure | Schiff Base |
| 3 | 118-58-1 | Benzoic acid, 2-hydroxy-, phenylmethyl ester | Benzyl Salicylate | Ester |
| 4 | 18127-01-0 | 4-(1,1-Dimethylethyl)benzenepropanal | Bourgeonal | Aldehyde |
| 5 | 65405-77-8 | Benzoic acid, 2-hydroxy-, 3-hexenyl ester, (Z)- | Cis-3-hexenyl Salicylate | Ester |
| 6 | 7492-67-3 | Acetaldehyde, [(3,7-dimethyl-6-octenyl)oxy]- | Citronellyl Oxyacetaldehyde | Acetaldehyde |
| 7 | 7775-00-0 | Propanal, 3-(4-isopropylphenyl)- | Cyclemax | Aldehyde |
| 8 | 25485-88-5 | Benzoic acid, 2-hydroxy-, cyclohexyl ester | Cyclohexyl Salicylate | Ester |
| 9 | 68738-94-3 | Octahydro-8,8-dimethylnaphthalene-2-carboxaldehyde | Cyclomyral ® | Aldehyde |
| 10 | 106-22-9 | dl-3,7-Dimethyl-6-octen-1-ol | Citronellol | Alcohol |
| 11 | 106-24-1 | trans-3,7-Dimethyl-2,6-octadien-1-ol | Geraniol | Alcohol |
| 12 | 84560-00-9 | Cyclopentan-1-ol, 2 Pentyl | Cyclopentol Hc 937165 | Alcohol |
| 13 | 103-95-7 | Benzenepropanal, .alpha.-methyl-4-(1-methylethyl)- | Cymal | Aldehyde |
| 14 | 30168-23-1 | Octahydro-4,7-methanoindanilydenebutanal | Dupical | Aldehyde |
| 15 | 10339-55-6 | 1,6-Nonadien-3-ol, 3,7-dimethyl- | Ethyl Linalool | Alcohol |
| 16 | 71077-31-1 | 4,8-Dimethyldeca-4,9-dienal | Floral Super | Aldehyde |
| 17 | 125109-85-5 | Benzenepropanal, .beta.-methyl-3-(1-methylethyl)- | Florhydral ® | Aldehyde |
| 18 | 63500-71-0 | 2-(2-Methylpropyl)-4-methyl-tetrahydro-2H-pyran-4-ol | Florol ® | Alcohol |
| 19 | 24237-00-1 | 2-Butyl-4,6-dimethyldihydropyran (isomers) | Gyrane | Pyran |
| 20 | 6259-76-3 | Benzoic acid, 2-hydroxy-, hexyl ester | Hexyl Salicylate | Ester |
| 21 | 1205-17-0 | 2-Methyl-3-(3,4-methylenedioxyphenyl)-propanal | Helional ™. | Aldehyde |
| 22 | 107-75-5 | Octanal, 7-hydroxy-3,7-dimethyl- | Hydroxycitronellal | Aldehyde |
| 23 | 78-70-6 | 1,6-Octadien-3-ol, 3,7-dimethyl- | Linalool | Alcohol |
| 24 | 31906-04-4 | 3-Cyclohexene-1-carboxaldehyde, 4-(4-hydroxy-4-methylpentyl)- | Lyral ® | Aldehyde |
| 25 | 103694-68-4 | 2,2-Dimethyl-3-(3-methylphenyl)-propanol | Majantol ® | Alcohol |
| 26 | 13828-37-0 | Cyclohexanemethanol, 4-(1-methylethyl)-, cis- | Mayol ® | Alcohol |
| 27 | 68991-97-9 | 2-Naphthaldehyde 1,2,3,4,5,6,7,8-octahydro-8,8-dimethyl- (mixture) | Melafleur | Aldehyde |
| 28 | 106-72-9 | 2,6-Dimethyl-5-heptenal | Melonal | Aldehyde |
| 29 | 63767-86-2 | 1-(4-Isopropylcyclohexyl)ethanol | Mugetanol | Alcohol |
| 30 | 56836-93-2 | 3-methyl-4-phenylbutan-2-ol | Muguesia | Alcohol |
| 31 | 13351-61-6 | Dimethyl phenyl Propanol | Muguetalcohol | Alcohol |
| 32 | 0300371-33-9 | 1H-Indene-ar-propanal. 2,3-dihydro-1,1-dimethyl- | 1H-Indene-ar-propanal. 2,3-dihydro-1,1-dimethyl- | Aldehyde |

TABLE 1-continued p-tert.Butyl-alpha-methyldihydrocinnamic aldehyde replacement materials (PRMs)

| Ingredient | CAS NUMBER | Chemical name | Trade Name | Chemical Type |
|---|---|---|---|---|
| 33 | 91-51-0 | Lilial/methyl anthranilate Schiff base | Verdantiol | Schiff Base |
| 34 | 10461-98-0 | 2-Cyclohexylidene-2-phenylacetonitrile | Peonile ® | Nitrile |
| 35 | 55066-48-3 | 3-Methyl-5-phenyl-1-pentanol | Phenoxanol ® | Alcohol |
| 36 | 215231-33-7 | 1-methyl-3-(2-methylpropyl)cyclohexan-1-ol | Rossitol ® | Alcohol |
| 37 | 6658-48-6 | 2-Methyl-3-(4-(2-methylpropyl)phenyl)propanal | Silvial ® | Aldehyde |
| 38 | 6658-48-6 | 3-(4-Isobutyl-phenyl)-2-methyl-propionaldehyde | Suzural | Aldehyde |
| 39 | 18479-57-7 | 2-Octanol, 2,6-dimethyl- | Tetrahydro Muguol ® | Alcohol |
| 40 | 78-69-3 | 3,7-Dimethyloctanol-3 | Tetrahydro Linalol | Alcohol |
| 41 | 84697-09-6 | 2-[(4-methylphenyl)methylene]-heptanal | Acalea | Aldehyde |
| 42 | 37172-53-5 | Methyl 2-hexyl-3-oxo-cyclopentanecarboxylate | Dihydro Iso Jasmonate | Ester |
| 43 | 101-86-0 | alpha-Hexylcinnamaldehyde | Hexyl Cinnamic Aldehyde | Aldehyde |
| 44 | 24851-98-7 | Cyclopentaneacetic acid, 2-oxo-2 Phenyl-, methyl ester | Hedione ® | Ester |
| 45 | 513-86-0 | (3-hydroxy-2-butanone) | Acetoin | Ketone |
| 46 | 141-13-9 | 2,6,10-Trimethyl-9-undecenal | Adoxal | Aldehyde |
| 47 | 207228-93-1 | 2-H 1,5-Benzodioxepin-3(4H)-one, 7 propyl- | Aldolone ® | Ketone |
| 48 | 211299-54-6 | 4H-4A, 9 Methanoazuleno (5,6 d)-1,3-dioxole, octahydro 2,2,5,8,8,9a-hexamethyl- | AMBROCENIDE ® | Azulene |
| 49 | 3738-00-9 | 3a,6,6,9a-Tetramethyl-dodecahydronaphtho[2,1-b]furan | Ambroxan | Furan |
| 50 | 362467-67-2 | 7(3-methyl butyl)-1,5-Benzodioxepin-3-one | Azurone ® | Ketone |
| 51 | 28219-61-6 | 2-Ethyl-4-(2,2,3-trimethylcyclopent-3-enyl-1)-2-buten-1-ol | Bacdanol ® | Alcohol |
| 52 | 28940-11-6 | 3,4-Dioxy(cycloacetonyl)toluene | Calone 1951 ®, | Ketone |
| 53 | 3738-00-9 | 3a,6,6,9a-Tetramethyl-dodecahydronaphtho[2,1-b]furan | Cetalox ® | Furan |
| 54 | 104-54-1 | 2-Propenol-1,3-phenyl- | Cinnamic alcohol | Alcohol |
| 55 | 5392-40-5 | 3,7-Dimethyl-2,6-octadienal | Citral | Aldehyde |
| 56 | 67634-20-2 | Hexahydro-4,7-methanoinden5(6)yl isobutyrate | Cyclabute | Ester |
| 57 | 5413-60-5 | Hexahydro-4,7-methanoinden-5(6)-yl acetate | Cyclacet ™ | Ester |
| 58 | 17511-60-3 | Hexahydro-4,7-methanoinden-5(6)-yl propionate | Cyclaprop ™ | Ester |
| 59 | 109-29-5 | Cyclohexadecanolide | Cyclohexadecanolide | Cyclic Ester |
| 60 | 3100-36-5 | 8-Cyclohexadecen-1-one | Cyclohexadecenone | Ketone |
| 61 | 507-72-7 | Cyclopentadecanone | Cyclopentadecanone | Cyclic Ketone |
| 62 | 57378-68-4 | 4-(2,6,6-Trimethyl-3-cyclohexen-1-yl)-but-3-en-4-one | Delta Damascone | Ketone |
| 63 | 67801-20-1 | 3-Methyl-5-(2,2,3-trimethyl-3-cyclopenten-1-yl)-4-penten-2-ol (& isomers) | Ebanol ® | Alcohol |
| 64 | 40910-49-4 | 1,6-Octadiene, 3-(1-ethoxyethoxy)-3,7-dimethyl- | Elintaal Forte | Acetal |
| 65 | 121-32-4 | Benzaldehyde, 3-ethoxy-4-hydroxy- | Ethyl Vanillin | Aldehyde |
| 66 | 105-95-3 | 1,4-Dioxacycloheptadecane-5,17-dione | Ethylene Brassylate | Cyclic Ester |
| 67 | 14595-54-1 | 4-Cyclopentadecen-1-one, (Z)- | Exaltenone 942008 | Cyclic Ketone |
| 68 | 106-02-5 | Oxacyclohexadecan-2-one | Exaltolide Total 935985 | Cyclic Ketone |
| 69 | 67634-14-4 | alpha,alpha-Dimethyl-p-ethylphenylpropanal | Floralozone | Aldehyde |
| 70 | 72903-27-6 | 1,4, Cyclohexanedicarboxylic acid, diethyl ester | Fructalate | Ester |
| 71 | 706-14-9 | gamma-Decalactone | Gamma Decalactone | Cyclic Ester |
| 72 | 111879-80-2 | Oxacyclohexadecen-2-one | Habanolide 100% | Ketone |
| 73 | 141773-73-1 | 1-Propanol, 2-[1-(3,3-dimethyl-cyclohexyl) ethoxy]-2-methyl-propanoate | Helvetolide ® | Cycloalkyl ester |
| 74 | 1222-05-5 | 1,3,4,6,7,8-Hexahydro-4,6,6,7,8,8-hexamethyl-cyclopenta-(g)-2-benzopyran | Hexamethylindanopyran | Pyran |
| 75 | 118562-73-5 | Cyclododecaneethanol, .beta.-methyl- | Hydroxyambran ® | Alcohol |
| 76 | 54464-57-2 | 3-Acetyl-3,4,10,10-tetramethylbicyclo[4.4.0]decane | Iso E Super ® | Ketone |
| 77 | 37677-14-8 | Isohexenyl cyclohexenyl carboxaldehyde | Iso Hexenyl Cyclohexenyl Carboxaldehyde | Aldehyde |
| 78 | 18871-14-2 | 4-Acetoxy-3-pentyl-2H-tetrahydropyran and isomers | Jasmal | Pyran |
| 79 | 198404-98-7 | (1-Methyl-2-(1,2,2-trimethylbicyclo[3.1.0]-hex-3-ylmethyl)cyclopropyl)methanol (Mixture of diastereoisomers) | Javanol ® | Alcohol |
| 80 | 112-54-9 | Dodecanal | Lauric Aldehyde | Aldehyde |

TABLE 1-continued p-tert.Butyl-alpha-methyldihydrocinnamic aldehyde replacement materials (PRMs)

| Ingredient | CAS NUMBER | Chemical name | Trade Name | Chemical Type |
|---|---|---|---|---|
| 81 | 55066-49-4 | gamma-Methyl benzenepentanal | Mefranal | Aldehyde |
| 82 | 63314-79-4 | 5-Cyclopentadecen-1-one, 3 Methyl- | Muscenone | Ketone |
| 83 | 1506-02-1 | 7-Acetyl-1,1,3,4,4,6-hexamethyltetralin | Tonalid ® II | Ketone |
| 84 | 95962-14-4 | 2-(2(4-Methyl-3-cyclohexen-1-yl)propyl)-cyclopentanone | Nectaryl ® | Ketone |
| 85 | 70788-30-6 | 1-(2,2,6-Trimethylcyclohexyl)hexanol-3 | Norlim Banol | Alcohol |
| 86 | 181258-87-7/181258-89-9 | 1-(1,1-dimethylpropyl)-4-ethoxycyclohexane (mixture of cis & trans isomers) | Ozofleur 29 Euro/kg | Ether |
| 87 | 5471-51-2 | 4-(4-Hydroxyphenyl)butanone-2 | Para Hydroxy Phenyl Butanone | Ketone |
| 88 | 33885-51-7 | 2-NORPINENE-2-PROPIONALDEHYDE,6,6-DIMETHYL | Pino Acetaldehyde | Aldehyde |
| 89 | 236391-76-7 | Acetic Acid, (1-oxopropoxy)-1-(3,3-dimethylcyclohexyl) ethyl ester | Romandolide ® | Ester |
| 90 | 28219-61-6 | 2-ethyl-4-(2,2,3-trimethyl-3-cyclopenten-1-yl)-2-buten-1-ol | Sanjinol | Alcohol |
| 91 | 109-29-5/507-72-7 | Cyclohexadecanolide and Cyclopentadecanone mixture | Silvanone ® Supra | Mixture Cyclyc Ester and Ketone |
| 92 | 8000-41-7 | Terpineol (alpha, beta, gamma) | Terpineol | Alcohol |
| 93 | 121-33-5 | Benzaldehyde, 4-hydroxy-3-methoxy- | Vanillin | Aldehyde |
| 94 | 37609-25-9 | 5-Cyclohexadecenone-1 | Velvione ® | Ketone |

Table 1 PRMs 1 to 44 are useful core materials that can reproduce the performance of p-tert.Butyl-alpha-methyldihydrocinnamic aldehyde in large number of applications, Table 1 PRMs 45 to 94 are useful supplementary materials that, when combined with one or more core materials, may provide the desired performance, when such core materials alone do not provide the desired performance.

Suitable p-tert.Butyl-alpha-methyldihydrocinnamic aldehyde mass replacement ratios for neat perfume compositions are expressed as:

$$\frac{\text{Replacement Material Mass Concentration}}{\text{p-tert.Butyl-alpha-methyldihydrocinnamic aldehyde Mass Concentration}}$$

TABLE 2 p-tert.Butyl-alpha-methyldihydrocinnamic aldehyde mass replacement ratios for neat perfume compositions

| Table 1 Material No. | Aspect 1 | Aspect 2 | Aspect 3 |
|---|---|---|---|
| 1 | 0.10-2.00 | 0.10-0.50 | 0.10-0.25 |
| 2 | 0.005-1.00 | 0.005-0.25 | 0.005-0.10 |
| 3 | 0.10-2.00 | 0.10-0.50 | 0.10-0.25 |
| 4 | 0.001-0.50 | 0.001-0.25 | 0.001-0.05 |
| 5 | 0.005-0.50 | 0.005-0.25 | 0.005-0.02 |
| 6 | 0.0001-0.05 | 0.0001-0.01 | 0.0001 to 0.005 |
| 7 | 0.0001-0.10 | 0.0001-0.05 | 0.0001-0.01 |
| 8 | 0.10-2.00 | 0.10-0.50 | 0.10-0.25 |
| 9 | 0.01-0.25 | 0.01-0.10 | 0.01-0.05 |
| 10 | 0.10-2.00 | 0.10-1.00 | 0.10-0.50 |
| 11 | 0.10-2.00 | 0.10-1.00 | 0.10-0.50 |
| 12 | 0.01-1.00 | 0.01-0.20 | 0.01-0.05 |
| 13 | 0.02-1.00 | 0.02-0.50 | 0.02-1.00 |
| 14 | 0.0001-0.05 | 0.0001-0.01 | 0.0001 to 0.005 |
| 15 | 0.10-1.00 | 0.1-0.50 | 0.1-0.20 |
| 16 | 0.0001-0.05 | 0.0001-0.01 | 0.0001 to 0.005 |
| 17 | 0.005-0.50 | 0.005-0.25 | 0.005-0.02 |
| 18 | 0.10-2.00 | 0.10-1.00 | 0.10-0.50 |

TABLE 2-continued p-tert.Butyl-alpha-methyldihydrocinnamic aldehyde mass replacement ratios for neat perfume compositions

| Table 1 Material No. | Aspect 1 | Aspect 2 | Aspect 3 |
|---|---|---|---|
| 19 | 0.005-0.25 | 0.005-0.10 | 0.005-0.05 |
| 20 | 0.10-2.00 | 0.10-0.50 | 0.10-0.25 |
| 21 | 0.10-2.00 | 0.10-1.00 | 0.10-0.50 |
| 22 | 0.10-2.00 | 0.10-1.00 | 0.10-0.50 |
| 23 | 0.10-2.00 | 0.10-0.50 | 0.10-0.25 |
| 24 | 0.10-1.00 | 0.10-0.75 | 0.10-0.25 |
| 25 | 0.02-1.00 | 0.02-0.50 | 0.02-1.00 |
| 26 | 0.02-1.00 | 0.02-0.50 | 0.02-1.00 |
| 27 | 0.02-1.00 | 0.02-0.50 | 0.02-1.00 |
| 28 | 0.0001-0.05 | 0.0001-0.01 | 0.0001 to 0.005 |
| 29 | 0.02-1.00 | 0.02-0.50 | 0.02-1.00 |
| 30 | 0.02-1.00 | 0.02-0.50 | 0.02-1.00 |
| 31 | 0.10-1.00 | 0.10-0.75 | 0.10-0.25 |
| 32 | 0.001-1.00 | 0.001-0.25 | 0.001-0.02 |
| 33 | 0.005-1.00 | 0.005-0.25 | 0.005-0.10 |
| 34 | 0.02-1.00 | 0.02-0.50 | 0.02-1.00 |
| 35 | 0.10-2.00 | 0.10-0.50 | 0.10-0.25 |
| 36 | 0.005-0.50 | 0.005-0.20 | 0.005-0.10 |
| 37 | 0.10-2.00 | 0.10-1.50 | 0.10-1.00 |
| 38 | 0.10-2.00 | 0.10-1.50 | 0.10-1.00 |
| 39 | 0.10-2.00 | 0.10-0.50 | 0.10-0.25 |
| 40 | 0.10-2.00 | 0.10-0.50 | 0.10-0.25 |
| 41 | 0.05-1.00 | 0.05-0.5 | 0.05-0.25 |
| 42 | 0.05-1.00 | 0.05-0.5 | 0.05-0.25 |
| 43 | 0.10-1.00 | 0.10-0.50 | 0.10-0.25 |
| 44 | 0.10-2.00 | 0.10-1.00 | 0.10-0.50 |
| 45 | 0.0001-0.05 | 0.0001-0.01 | 0.0001 to 0.005 |
| 46 | 0.0001-0.05 | 0.0001-0.01 | 0.0001 to 0.005 |
| 47 | 0.001-0.25 | 0.001-0.10 | 0.001 to 0.05 |
| 48 | 0.001-0.50 | 0.001-0.25 | 0.001-0.02 |
| 49 | 0.001-0.50 | 0.001-0.25 | 0.001-0.02 |
| 50 | 0.001-0.25 | 0.001-0.10 | 0.001 to 0.05 |
| 51 | 0.05-2.00 | 0.05-0.5 | 0.05-0.20 |
| 52 | 0.0001-0.25 | 0.0001-0.10 | 0.0001 to 0.05 |
| 53 | 0.001-0.50 | 0.001-0.25 | 0.001-0.02 |
| 54 | 0.001-0.50 | 0.001-0.25 | 0.001-0.05 |
| 55 | 0.001-0.50 | 0.001-0.25 | 0.001-0.02 |
| 56 | 0.02-1.00 | 0.02-0.50 | 0.02-0.20 |
| 57 | 0.02-1.00 | 0.02-0.50 | 0.02-0.20 |
| 58 | 0.02-1.00 | 0.02-0.50 | 0.02-0.20 |

TABLE 2-continued p-tert.Butyl-alpha-methyldihydrocinnamic aldehyde mass replacement ratios for neat perfume compositions

| Table 1 Material No. | Aspect 1 | Aspect 2 | Aspect 3 |
|---|---|---|---|
| 59 | 0.05-1.00 | 0.05-0.5 | 0.05-0.20 |
| 60 | 0.05-1.00 | 0.05-0.5 | 0.05-0.20 |
| 61 | 0.05-1.00 | 0.05-0.5 | 0.05-0.20 |
| 62 | 0.0001-0.25 | 0.0001-0.10 | 0.0001 to 0.05 |
| 63 | 0.05-1.00 | 0.01-0.50 | 0.01-0.20 |
| 64 | 0.0001-0.10 | 0.0001-0.05 | 0.0001-0.01 |
| 65 | 0.0001-0.05 | 0.0001-0.01 | 0.0001 to 0.005 |
| 66 | 0.05-0.50 | 0.005-0.30 | 0.05-0.20 |
| 67 | 0.05-1.00 | 0.05-0.5 | 0.05-0.20 |
| 68 | 0.05-1.00 | 0.05-0.5 | 0.05-0.20 |
| 69 | 0.001-0.50 | 0.001-0.25 | 0.001-0.05 |
| 70 | 0.002-0.5 | 0.002-0.25 | 0.002-0.05 |
| 71 | 0.005-0.50 | 0.005-0.25 | 0.005-0.10 |
| 72 | 0.05-1.00 | 0.05-0.5 | 0.05-0.20 |
| 73 | 0.010-1.00 | 0.01-0.50 | 0.01-0.20 |
| 74 | 0.05-1.00 | 0.05-0.5 | 0.05-0.20 |
| 75 | 0.001-0.50 | 0.001-0.25 | 0.001-0.02 |
| 76 | 0.05-2.00 | 0.05-0.5 | 0.05-0.20 |
| 77 | 0.01-0.25 | 0.01-0.10 | 0.01-0.05 |
| 78 | 0.01-0.50 | 0.01-0.20 | 0.01-0.10 |
| 79 | 0.001-0.50 | 0.001-0.25 | 0.001-0.02 |
| 80 | 0.0001-0.05 | 0.0001-0.01 | 0.0001 to 0.005 |
| 81 | 0.0001-0.10 | 0.0001-0.05 | 0.0001-0.01 |
| 82 | 0.0001-0.05 | 0.0001-0.01 | 0.0001 to 0.005 |
| 83 | 0.0001-0.10 | 0.0001-0.05 | 0.0001-0.01 |
| 84 | 0.005-0.50 | 0.005-0.25 | 0.005-0.10 |
| 85 | 0.001-0.50 | 0.001-0.25 | 0.001-0.02 |
| 86 | 0.0001-0.10 | 0.0001-0.05 | 0.0001-0.01 |
| 87 | 0.0001-0.05 | 0.0001-0.01 | 0.0001 to 0.005 |
| 88 | 0.0001-0.05 | 0.0001-0.01 | 0.0001 to 0.005 |
| 89 | 0.05-1.00 | 0.05-0.5 | 0.05-0.20 |
| 90 | 0.05-1.00 | 0.01-0.5 | 0.01-0.20 |
| 91 | 0.05-1.00 | 0.05-0.5 | 0.05-0.20 |
| 92 | 0.10-2.00 | 0.10-0.50 | 0.10-0.25 |
| 93 | 0.0001-0.05 | 0.0001-0.01 | 0.0001 to 0.005 |
| 94 | 0.05-1.00 | 0.05-0.5 | 0.05-0.20 |

The replacement levels disclosed in Table 2 above may result in a neat perfume having substantially the same performance, for example, one or more of the following benefits at a level that is desired: neat product odor; wet fabric odor when applied to a fabric; dry fabric odor when applied to a fabric; reduced leakage from an encapsulate, including an encapsulate such as a perfume microcapsule; increased head space versus neat oil in certain perfume delivery technologies; odor when used in a matrix perfume delivery that is applied to a package; neat product odor when applied to a cleaning and/or treatment composition; fine fragrance composition odor when used in a fine fragrance; dry hair odor when a composition comprising such a composition is applied to hair; perfume bloom from a solution comprising such a composition and character when applied to a situs. Confirmation of such benefits can be obtained by applying standard test methodologies.

In one aspect, a suitable perfume composition employing the aforementioned replacement technology may be A perfume comprising essentially zero weight percent p-tert.Butyl-alpha-methyldihydrocinnamic aldehyde, or even zero weight percent p-tert.Butyl-alpha-methyldihydrocinnamic aldehyde and from about 0.01 to about 80, from about 0.01 to about 40, from about 0.01 to about 18 or even from about 0.01 to about 7 weight percent of a cocktail selected from:

a) a cocktail comprising, based on total cocktail weight, from about 0.01 to about 10, from about 0.01 to about 5 or even from about 0.01 to about 2 weight percent Octahydro-4,7-methanoindanilydenebutanal and from about 0.001 to about 5, from about 0.001 to about 2 or even from about 0.001 to about 0.5 weight percent 4,8-Dimethyldeca-4,9-dienal;

b) a cocktail comprising, based on total cocktail weight, from about 0.1 to about 50, from about 0.1 to about 25 or even from about 0.1 to about 10 weight percent Benzenepropanal, beta.-methyl-3-(1-methylethyl)-, and from about 0.1 to about 20, from about 0.1 to 5 about or even from about 0.01 to about 1 weight percent Isohexenyl cyclohexenyl carboxaldehyde;

c) a cocktail comprising, based on total cocktail weight, from about 0.1 to about 50, from about 0.1 to about 25 or even from about 0.1 to about 10 weight percent Benzenepropanal, .alpha.-methyl-4-(1-methylethyl)- and from about 10 to about 100, from about 50 to 100 about or even from about 75 to about 100 weight percent 2-(2-Methylpropyl)-4-methyl-tetrahydro-2H-pyran-4-ol;

d) a cocktail comprising, based on total cocktail weight, from about 0.001 to about 5, from about 0.001 to about 1.0 or even from about 0.001 to about 0.1 weight percent Acetaldehyde, [(3,7-dimethyl-6-octenyl)oxy]- and from about 0.1 to about 75, from about 0.1 to 25 about or even from about 0.1 to about 5 weight percent Benzenepropanal, .alpha.-methyl-4-(1-methylethyl)- and from about 25 to about 100, from about 50 to 100 about or even from about 75 to about 100 weight percent Octanal, 7-hydroxy-3,7-dimethyl-;

e) a cocktail comprising, based on total cocktail weight, from about 0.001 to about 5, from about 0.001 to about 1 or even from about 0.001 to about 0.1 weight percent Acetaldehyde, [(3,7-dimethyl-6-octenyl)oxy]- and from about 0.1 to about 75, from about 0.1 to 25 about or even from about 0.1 to about 5 weight percent Benzenepropanal, .alpha.-methyl-4-(1-methylethyl)- and from about 25 to about 100, from about 50 to 100 about or even from about 75 to about 100 weight percent Benzoic acid, 2-hydroxy-, hexyl ester;

f) a cocktail comprising, based on total cocktail weight, from about 10 to about 100, from about 10 to about 75 or even from about 10 to about 50 weight percent Benzoic acid, 2-hydroxy-, phenylmethyl ester, and from about 0.1 to about 50, from about 0.1 to 25 about or even from about 0.1 to about 5 weight percent 4-(1,1-Dimethylethyl) benzenepropanal and from about 0.1 to about 50 from about 0.1 to 25 about or even from about 0.1 to about 10 weight percent Octahydro-8,8-dimethylnaphthalene-2-carboxaldehyde and from about 0.1 to about 75, from about 0.1 to 50 about or even from about 0.1 to about 20 weight percent Benzenepropanal, alpha.-methyl-4-(1-methylethyl)-, and from about 1.0 to about 75, from about 1.0 to 50 about or even from about 1.0 to about 25 weight percent Benzoic acid, 2-hydroxy-, hexyl ester and from about 0.1 to about 75, from about 0.1 to 50 about or even from about 0.1 to about 25 weight percent 1,6-Octadien-3-ol, 3,7-dimethyl-, and from about 0.1 to about 75, from about 0.1 to 50 about or even from about 0.1 to about 20 weight percent 3-Cyclohexene-1-carboxaldehyde, 4-(4-hydroxy-4-methylpentyl)-, and from about 0.1 to about 20, from about 0.1 to 5 about or even from about 0.01 to about 1 weight percent 2,6-Dimethyl-5-heptenal, and from about 0.1 to about 75, from about 0.1 to 50 about or even from about 0.1 to about 10 weight percent 2-Cyclohexylidene-2-phenylacetonitrile, and from about 0.1 to about 10, from about 0.1 to 5 about or even from about 0.001 to about 0.5 weight percent 3-hydroxy-2-butanone;

g) a cocktail comprising, based on total cocktail weight, from about 1.0 to about 75, from about 5 to about 50 or even from about 5 to about 25 weight percent n-Pentyl salicylate and from about 1 to about 75, from about 5 to 50 about or even from about 10 to about 20 weight percent Benzoic acid, 2-hydroxy-, phenylmethyl ester and from about 0.1 to about 25, from about 0.1 to 10 about or even from about 0.5 to about 5 weight percent Benzoic acid, 2-hydroxy-, 3-hexenyl ester, (Z)—, and from about 1 to about 75, from about 5 to 50 about or even from about 10 to about 20 weight percent Benzoic acid, 2-hydroxy-, cyclohexyl ester and from about 0.1 to about 20, from about 0.1 to 5 about or even from about 0.01 to about 2 weight percent Octahydro-4,7-methanoindanilydenebutanal, and from about 0.1 to about 20, from about 0.1 to 5 about or even from about 0.01 to about 1 weight percent 4,8-Dimethyldeca-4,9-dienal and from about 1 to about 75, from about 5 to 50 about or even from about 10 to about 25 weight percent Benzoic acid, 2-hydroxy-, hexyl ester and from about 1.0 to about 75, from about 5 to 50 about or even from about 10 to about 25 weight percent Hexahydro-4,7-methanoinden5(6)yl isobutyrate;

h) a cocktail comprising, based on total cocktail weight, from about 1.0 to about 75, from about 5 to about 50 or even from about 10 to about 20 weight percent n-Pentyl salicylate and from about 1 to about 75, from about 5 to 50 about or even from about 10 to about 20 weight percent Benzoic acid, 2-hydroxy-, phenylmethyl ester and from about 1 to about 50, from about 0.1 to 10 about or even from about 0.1 to about 5 weight percent Benzoic acid, 2-hydroxy-, 3-hexenyl ester, (Z)—, and from about 1 to about 75, from about 5 to 50 about or even from about 10 to about 20 weight percent Benzoic acid, 2-hydroxy-, cyclohexyl ester, and from about 0.1 to about 25, from about 0.1 to 10 about or even from about 0.1 to about 5 weight percent Octahydro-8,8-dimethylnaphthalene-2-carboxaldehyde and from about 0.1 to about 20, from about 0.1 to 5 about or even from about 0.01 to about 2 weight percent Octahydro-4,7-methanoindanilydenebutanal and from about 0.1 to about 20, from about 0.1 to 5 about or even from about 0.01 to about 1 weight percent 4,8-Dimethyldeca-4,9-dienal and from about 1 to about 75, from about 5 to 50 about or even from about 10 to about 20 weight percent Benzoic acid, 2-hydroxy-, hexyl ester and from about 1 to about 75, from about 5 to 50 about or even from about 10 to about 20 weight percent 1,6-Octadien-3-ol, 3,7-dimethyl-, and from about 0.1 to about 50, from about 0.1 to 25 about or even from about 0.1 to about 5 weight percent Cyclohexanemethanol, 4-(1-methylethyl)-, cis-, and from about 0.1 to about 20, from about 0.1 to 5 about or even from about 0.01 to about 1 weight percent 2,6-Dimethyl-5-heptenal, and from about 0.1 to about 50, from about 0.1 to 25 about or even from about 0.1 to about 5 weight percent 2-Cyclohexylidene-2-phenylacetonitrile, and from about 0.1 to about 80 from about 0.1 to 25 about or even from about 1 to about 5 weight percent alpha-Hexylcinnamaldehyde, and from about 0.1 to about 50, from about 0.1 to 25 about or even from about 1 to about 5 weight percent Hexahydro-4,7-methanoinden5(6)yl isobutyrate, and from about 1 to about 75, from about 1 to 50 about or even from about 10 to about 20 weight percent 1,4-Dioxacycloheptadecane-5,17-dione, and from about 0.1 to about 5, from about 0.1 to 1 about or even from about 0.01 to about 0.5 weight percent Benzaldehyde, 4-hydroxy-3-methoxy-;

i) a cocktail comprising, based on total cocktail weight, from about 1 to about 75 from about 5 about 50 even from about 10 to about 20 weight percent Cyclohexanemethanol, 4-(1-methylethyl)-, cis-, and from about 1 to about 75, from about 5 to 50 about or even from about 10 to about 20 weight percent 2-Naphthaldehyde, 1,2,3,4,5,6,7,8-octahydro-8,8-dimethyl-(mixture), and from about 5 to about 90, from about 10 to 75 about or even from about 25 to about 50 weight percent 2-Octanol, 2,6-dimethyl-, and from about 1 to about 75, from about 5 to 50 about or even from about 10 to about 25 weight percent Methyl 2-hexyl-3-oxo-cyclopentanecarboxylate;

j) a cocktail comprising, based on total cocktail weight, from about 0.1 to about 50, from about 0.1 to about 10 or even from about 0.1 to about 5 weight percent 4-(1,1-Dimethylethyl)benzenepropanal and from about 0.1 to about 20, from about 0.1 to 5 about or even from about 0.1 to about 1 weight percent Octahydro-8,8-dimethylnaphthalene-2-carboxaldehyde and from about 1 to about 75, from about 5 to 50 about or even from about 10 to about 20 weight percent Benzenepropanal, alpha.-methyl-4-(1-methylethyl)-, and from about 0.1 to about 20, from about 0.1 to 5 about or even from about 0.01 to about 1 weight percent Benzenepropanal, .beta.-methyl-3-(1-methylethyl)-, and from about 1 to about 75, from about 5 to 50 about or even from about 10 to about 25 weight percent Benzoic acid, 2-hydroxy-, hexyl ester, and from about 1 to about 75, from about 5 to 50 about or even from about 10 to about 20 weight percent 3-Cyclohexene-1-carboxaldehyde, 4-(4-hydroxy-4-methylpentyl)-, and from about 0.1 to about 20, from about 0.1 to 5 about or even from about 0.01 to about 1 weight percent 2,6-Dimethyl-5-heptenal, and from about 1 to about 75, from about 5 to 50 about or even from about 10 to about 20 weight percent Cyclopentaneacetic acid, 2-oxo-2 Phenyl-, methyl ester, and from about 1 to about 75 from about 5 to 50 about or even from about 10 to about 20 weight percent Hexahydro-4,7-methanoinden5(6)yl isobutyrate, and from about 1 to about 75, from about 5 to 50 about or even from about 10 to about 25 weight percent 3-Acetyl-3,4,10,10-tetramethylbicyclo[4.4.0]decane, and from about 0.01 to about 7.5, from about 0.01 to 5 about or even from about 0.01 to about 1 weight percent Dodecanal, and from about 0.1 to about 50, from about 0.1 to 5 about or even from about 0.1 to about 1 weight percent 2-(2(4-Methyl-3-cyclohexen-1-yl)propyl)-cyclopentanone, and from about 0.001 to about 5, from about 0.001 to 2 about or even from about 0.001 to about 1 weight percent 4-(4-Hydroxyphenyl)butanone-2;

k) a cocktail comprising, based on total cocktail weight, from about 0.1 to about 50, from about 0.1 to about 10 or even from about 0.1 to about 5 weight percent Benzoic acid, 2-[(7-hydroxy-3,7-dimethyloctylidene)amino]-, methyl, and from about 1 to about 75, from about 5 to 50 about or even from about 10 to about 20 weight percent 1,6-Octadien-3-ol, 3,7-dimethyl-, and from about 0.1 to about 25, from about 0.1 to 10 about or even from about 0.1 to about 5 weight percent Cyclohexanemethanol, 4-(1-methylethyl)-, cis-, and from about 0.01 to about 20, from about 0.01 to 5 about or even from 0.01 about to about 1 weight percent 2,6-Dimethyl-5-heptenal, and from about 0.01 to about 20, from about 0.01 to 5 about or even from about 0.01 to about 1 weight percent 2,6,10-Trimethyl-9-undecenal, and from about 0.1 to about 25, from about 0.1 to 10 about or even from about 0.1 to about 5 weight percent gamma-Decalactone, and from about 1 to about 90, from about 1 to 50 about or even from about 1 to about 10 weight percent Isohexenyl cyclohexenyl carboxaldehyde;

l) a cocktail comprising, based on total cocktail weight, from about 0.1 to about 50, from about 0.1 to about 25 or even from about 0.1 to about 10 weight percent 4-(1,1-Dimethylethyl)benzenepropanal, and from about 0.1 to about 75, from about 0.1 to 50 about or even about from 0.1 to about 10 weight percent Benzenepropanal, alpha.-methyl-4-(1-methylethyl)-, and from about 10 to about 95, from about 10 to 75 about or even from about 10 to about 50 weight percent 3-(4-Isobutyl-phenyl)-2-methyl-propionaldehyde;

m) and mixtures thereof.

The PRMs disclosed in Table 1 above and stereoisomers of such PRMs can be obtained from: IFF Global Headquarters, 521 West 57th Street New York, N.Y. 10019, United States; Givaudan SA (Corporate), 5, Chemin de la Parfumerie, 1214 Vernier; Firmenich S A, Route des Jeunes 1, P.O. Box 239, Genève 8 CH-1211, Switzerland; Takasago Internatinal Corporation, Nissey Aroma Square 17F, 5-37-1, Kamata, Ohta-ku, Tokyo; and Symrise AG 1 37603 Holzminden Germany Additional adjunct PRMs may be useful in forming neat perfumes when p-tert.Butyl-alpha-methyldihydrocinnamic aldehyde is replaced in whole or in part by a replacement material/composition disclosed in the present specification. Suitable adjunct PRMs include acetals, alcohols, aldeyhdes, alkene, azulenes, cyclic esters, cyclic ketones, esters, ethers, furans, ketones, lactones, pyrans, nitrites and Schiffs bases. Such adjunct PRMs are in addition to the replacement materials/compositions disclosed herein. For example if a neat perfume composition comprises 1% p-tert.Butyl-alpha-methyldihydrocinnamic aldehyde and 1% of Table 1 Material No. 18 having the chemical name 2-(2-Methylpropyl)-4-methyl-tetrahydro-2H-pyran-4-ol, the neat perfume wherein p-tert.Butyl-alpha-methyldihydrocinnamic aldehyde is replaced would comprise 2% of Table 1 Material No. 18.

Examples of suitable adjunct aldehyde PRMs include but are not limited to: alpha-Amylcinnamaldehyde, Anisic Aldehyde, Decyl Aldehyde, Lauric aldehyde, Methyl n-Nonyl acetaldehyde, Methyl octyl acetaldehyde, Nonylaldehyde, Benzenecarboxaldehyde, Neral, Geranial, 2,6 octadiene, 1,1 diethoxy-3,7-dimethyl-, 4-Isopropylbenzaldehyde, 2,4-Dimethyl-3-cyclohexene-1-carboxaldehyde, alpha-Methyl-p-isopropyldihydrocinnamaldehyde, 3-(3-isopropylphenyl) butanal, alpha-Hexylcinnamaldehyde, 7-Hydroxy-3,7-dimethyloctan-1-al, 2,4-Dimethyl-3-Cyclohexene-1-carboxaldehyde, Octyl Aldehyde, Phenylacetaldehyde, 2,4-Dimethyl-3-Cyclohexene-1-carboxaldehyde, Hexanal, 3,7-Dimethyloctanal, 6,6-Dimethylbicyclo[3.1.1]hept-2-ene-2-butanal, Nonanal, Octanal, 2-Nonenal Undecenal, 2-Methyl-4-(2,6,6-trimethyl-1-cyclohexenyl-1)-2-butenal, 2,6-Dimethyloctanal3-(p-Isopropylphenyl)propionaldehyde, 3-Phenyl-4-pentenal Citronellal, o/p-Ethyl-alpha,alpha-, 9-Decenal, dimethyldihydrocinnamaldehyde, p-Isobutyl-alpha-methylydrocinnamaldehyde, cis-4-Decen-1-al, 2,5-Dimethyl-2-ethenyl-4-hexenal, trans-2-Methyl-2-butenal, 3-Methylnonanal, alpha-Sinensal, 3-Phenylbutanal, 2,2-Dimethyl-3-phenylpropionaldehyde, m-tert.Butyl-alpha-methyldihydrocinnamic aldehyde, Geranyl oxyacetaldehyde, trans-4-Decen-1-al, Methoxycitronellal and mixtures thereof.

Examples of suitable adjunct Ester PRMs include but are not limited to: Allyl cyclohexanepropionate, Allyl heptanoate, Allyl Amyl Glycolate, Allyl caproate, Amyl acetate (n-Pentyl acetate), Amyl Propionate, Benzyl acetate, Benzyl propionate, Benzyl salicylate, cis-3-Hexenylacetate, Citronellyl acetate, Citronellyl propionate, Cyclohexyl salicylate, Dihydro Isojasmonate Dimethyl benzyl carbinyl acetate, Ethyl acetate, Ethyl acetoacetate, Ethyl Butyrate, Ethyl-2-methyl butryrate, Ethyl-2-methyl pentanoate Fenchyl acetate (1,3,3-Trimethyl-2-norbornanyl acetate), Tricyclodecenyl acetate, Tricyclodecenyl propionate, Geranyl acetate, cis-3-Hexenyl isobutyrate, Hexyl acetate, cis-3-Hexenyl salicylate, n-Hexyl salicylate, Isobornyl acetate, Linalyl acetate, p-t-Butyl Cyclohexyl acetate, (−)-L-Menthyl acetate, o-t-Butylcyclohexyl acetate), Methyl benzoate, Methyl dihydro iso jasmonate, alpha-Methylbenzyl acetate, Methyl salicylate, 2-Phenylethyl acetate, Prenyl acetate, Cedryl acetate, Cyclabute, Phenethyl phenylacetate, Terpinyl formate, Citronellyl anthranilate, Ethyl tricyclo[5.2.1.0-2,6]decane-2-carboxylate, n-Hexyl ethyl acetoacetate, 2-tert.-Butyl-4-methyl-cyclohexyl acetate, Formic acid, 3,5,5-trimethylhexyl ester, Phenethyl crotonate, Cyclogeranyl acetate, Geranyl crotonate, Ethyl geranate, Geranyl isobutyrate, Ethyl 2-nonynoate-2,6-Octadienoic acid, 3,7-dimethyl-, methyl ester, Citronellyl valerate, 2-Hexenylcyclopentanone, Cyclohexyl anthranilate, L-Citronellyl tiglate, Butyl tiglate, Pentyl tiglate, Geranyl caprylate, 9-Decenyl acetate, 2-Isopropyl-5-methylhexyl-1 butyrate, n-Pentyl benzoate, 2-Methylbutyl benzoate (mixture with pentyl benzoate), Dimethyl benzyl carbinyl propionate, Dimethyl benzyl carbinyl acetate, trans-2-Hexenyl salicylate, Dimethyl benzyl carbinyl isobutyrate, 3,7-Dimethyloctyl formate, Rhodinyl formate, Rhodinyl isovalerate, Rhodinyl acetate, Rhodinyl butyrate, Rhodinyl propionate, Cyclohexylethyl acetate, Neryl butyrate, Tetrahydrogeranyl butyrate, Myrcenyl acetate, 2,5-Dimethyl-2-ethenylhex-4-enoic acid, methyl ester, 2,4-Dimethylcyclohexane-1-methyl acetate, Ocimenyl acetate, Linalyl isobutyrate, 6-Methyl-5-heptenyl-1 acetate, 4-Methyl-2-pentyl acetate, n-Pentyl 2-methylbutyrate, Propyl acetate, Isopropenyl acetate, Isopropyl acetate, 1-Methylcyclohex-3-enecarboxylic acid, methyl ester, Propyl tiglate, Propyl/isobutyl cyclopent-3-enyl-1-acetate (alpha-vinyl), Butyl 2-furoate, Ethyl 2-pentenoate, (E)-Methyl 3-pentenoate, 3-Methoxy-3-methylbutyl acetate, n-Pentyl crotonate, n-Pentyl isobutyrate, Propyl formate, Furfuryl butyrate, Methyl angelate, Methyl pivalate, Prenyl caproate, Furfuryl propionate, Diethyl malate, Isopropyl 2-methylbutyrate, Dimethyl malonate, Bornyl formate, Styralyl acetate, 1-(2-Furyl)-1-propanone, 1-Citronellyl acetate, 3,7-Dimethyl-1,6-nonadien-3-yl acetate, Neryl crotonate, Dihydromyrcenyl acetate, Tetrahydromyrcenyl acetate, Lavandulyl acetate, 4-Cyclooctenyl isobutyrate, Cyclopentyl isobutyrate, 3-Methyl-3-butenyl acetate, Allyl acetate, Geranyl formate, cis-3-Hexenyl caproate and mixtures thereof.

Examples of suitable adjunct Alcohol PRMs include but are not limited to: Benzyl alcohol, beta-gamma-Hexenol (2-Hexen-1-ol), Cedrol, Citronellol, Cinnamic alcohol, p-Cresol, Cumic alcohol, Dihydromyrcenol, 3,7-Dimethyl-1-octanol, Dimethyl benzyl carbinol, Eucalyptol, Eugenol, Fenchyl alcohol, Geraniol, Hydratopic alcohol, Isononyl alcohol (3,5,5-Trimethyl-1-hexanol), Linalool, Methyl Chavicol (Estragole), Methyl Eugenol (Eugenyl methyl ether), Nerol, 2-Octanol, Patchouli alcohol, Phenyl Hexanol (3-Methyl-5-phenyl-1-pentanol), Phenethyl alcohol, alpha-Terpineol, Tetrahydrolinalool, Tetrahydromyrcenol, 4-methyl-3-decen-5-ol, 1-3,7-Dimethyloctane-1-ol, 2-(Furfuryl-2)-heptanol, 6,8-Dimethyl-2-nonanol, Ethyl norbornyl cyclohexanol, beta-Methyl cyclohexane ethanol, 3,7-Dimethyl-(2),6-octen(adien)-1-ol, trans-2-Undecen-1-ol 2-Ethyl-2-prenyl-3-hexenol, Isobutyl benzyl carbinol, Dimethyl benzyl carbinol, Ocimenol, 3,7-Dimethyl-1,6-nonadien-3-ol (cis & trans), Tetrahydromyrcenol, alpha-Terpineol, 9-Decenol-1,2 (Hexenyl)cyclopentanol, 2,6-Dimethyl-2-heptanol, 3-Methyl-1-octen-3-ol, 2,6-Dimethyl-5-hepten-2-ol, 3,7,9-Trimethyl-1,6-decadien-3-ol, 3,7-Dimethyl-6-nonen-1-ol, 3,7-Dimethyl-1-octyn-3-ol, 2,6-Dimethyl-1,5,7-octatrienol-3, Dihydromyrcenol, 2,6,10-Trimethyl-5,9-undecadienol, 2,5-Dimethyl-2-propylhex-4-enol-1,(Z), 3-Hexenol, o,m,p-Methylphenylethanol, 2-Methyl-5-phenyl-1-pentanol, 3-Methylphenethyl alcohol, para-Methyl dimethyl benzyl carbinol, Methyl benzyl carbinol, p-Methylphenylethanol, 3,7-Dimethyl-2-octen-1-ol, 2-Methyl-6-methylene-7-octen-4-ol and mixtures thereof.

Examples of suitable adjunct Ketone PRMs include but are not limited to Oxacycloheptadec-10-en-2-one, Benzylacetone, Benzophenone, L-Carvone, cis-Jasmone, 4-(2,6,6-Trimethyl-3-cyclohexen-1-yl)-but-3-en-4-one, Ethyl amyl ketone, alpha-Ionone, Ionone Beta, Ethanone, Octahydro-2,3,8,8-tetramethyl-2-acetonaphthalene, alpha-Irone, 1-(5,5-Dimethyl-1-cyclohexen-1-yl)-4-penten-1-one, 3-Nonanone, Ethyl hexyl ketone, Menthone, 4-Methylacetophenone, gamma-Methyl Ionone Methyl pentyl ketone, Methyl Heptenone (6-Methyl-5-hepten-2-one), Methyl Heptyl ketone, Methyl Hexyl ketone, delta Muscenone, 2-Octanone, 2-Pentyl-3-methyl-2-cyclopenten-1-one, 2-Heptylcyclopentanone, alpha-Methylionone, 3-Methyl-2-(trans-2-pentenyl)-cyclopentenone, Octenyl cyclopentanone, n-Amylcyclopentenone, 6-Hydroxy-3,7-dimethyloctanoic acid lactone, 2-Hydroxy-2-cyclohexen-1-one, 3-Methyl-4-phenyl-3-buten-2-one, 2-Pentyl-2,5,5-trimethylcyclopentanone, 2-Cyclopentylcyclopentanol-1,5-Methylhexan-2-one, gamma-Dodecalactone, delta-Dodecalactone delta-Dodecalactone, gamma-Nonalactone, delta-Nonalactone, gamma-Octalactone, delta-Undecalactone, gamma-Undecalactone, and mixtures thereof.

Examples of suitable adjunct Ether PRMs include but are not limited to: p-Cresyl methyl ether, 4,6,6,7,8,8-Hexamethyl-1,3,4,6,7,8-hexahydro-cyclopenta(G)-2-benzopyran, beta-Naphthyl methyl ether, Methyl Iso Butenyl Tetrahydro Pyran, (Phantolide) 5-Acetyl-1,1,2,3,3,6 hexamethylindan, (Tonalid™)-7-Acetyl-1,1,3,4,4,6-hexamethyltetralin, 2-Phenylethyl 3-methylbut-2-enyl ether, Ethyl geranyl ether, Phenylethyl isopropyl ether and mixtures thereof.

Examples of suitable adjunct Alkene PRMs include but are not limited to: Allo-Ocimene, Camphene, beta-Caryophyllene, Cadinene, Diphenylmethane, d-Limonene, Lymolene, beta-Myrcene, Para-Cymene, alpha-Pinene, beta-Pinene, alpha-Terpinene, gamma-Terpinene, Terpineolene, 7-Methyl-3-methylene-1,6-octadiene and mixtures thereof.

Examples of suitable adjunct Nitrile PRMs include but are not limited to: 3,7-Dimethyl-6-octenenitrile, 3,7-Dimethyl-2 (3), 6-nonadienenitrile, (2E,6Z) 2,6-nonadienenitrile, n-dodecane nitrile.

Examples of suitable adjunct Schiffs Bases PRMs include but are not limited to: Citronellyl nitrile, Nonanal/methyl anthranilate, Anthranilic acid, N-octylidene-, methyl ester (L)-, Hydroxycitronellal/methyl anthranilate, 2-Methyl-3-(4-Cyclamen aldehyde/methyl anthranilate, methoxyphenyl propanal/Methyl anthranilate, Ethyl p-aminobenzoate/hydroxycitronellal, Citral/methyl anthranilate, 2,4-Dimethylcyclohex-3-enecarbaldehyde methyl anthranilate, Hydroxycitronellal-indole and mixtures thereof.

Perfume compositions comprising the replacements for p-tert.Butyl-alpha-methyldihydrocinnamic aldehyde, as disclosed in the present specification may be used at the same levels in perfume delivery systems and/or consumer products, including cleaning and/or treatment compositions, including fabric and/or hard surface cleaning and/or treatment compositions including detergents and compacted forms of same as used in such products, prior to implementing the change to such replacement materials.

In one aspect, the perfumes comprising the replacement materials disclosed in Table 1 and stereoisomers thereof are suitable for use, as defined by the present specification, in consumer products at levels, based on total consumer product weight of from about 0.0001% to about 100%, 0.0001% to about 25%, from about 0.0005% to about 10%, from about 0.001% to about 5%, from about 0.005% to about 2.5%, or even from 0.01% to about 1%.

In one aspect, the perfumes comprising the replacement materials disclosed in Table 1 and stereoisomers thereof are suitable for use, as defined by the present specification, in cleaning and/or treatment composition at levels, based on total cleaning and treatment products weight of from about 0.0001% to about 25%, from about 0.0005% to about 10%, from about 0.001% to about 5%, from about 0.005% to about 2.5%, or even from 0.01% to about 1%.

In one aspect, the perfumes comprising the replacement materials disclosed in Table 1 and stereoisomers thereof are suitable for use, as defined by the present specification, in fabric and/or hard surface cleaning and/or treatment compositions at levels, based on total fabric and/or hard surface cleaning and/or treatment composition weight of from about 0.00001% to about 25%, from 0.00005% to about 10%, from 0.0001% to about 5%, from 0.0005% to about 1.0%, or even from 0.001% to about 0.5%.

In one aspect, a detergent that may comprise the same level of perfume as disclosed for the aforementioned fabric and hard surface cleaning and/or treatment compositions is disclosed.

In one aspect, the perfumes comprising the replacement materials disclosed in Table 1 and stereoisomers thereof are suitable for use, in highly compacted consumer products, including highly compacted fabric and hard surface cleaning and/or treatment compositions, for example highly compacted detergents that may be solids or fluids, at levels, based on total composition weight, of from about 0.00001% to about 25%, from 0.00005% to about 10%, from 0.0001% to about 5%, from 0.0005% to about 1.0%, or even from 0.001% to about 0.5%.

Perfume Delivery Systems

Certain perfume delivery systems, methods of making certain perfume delivery systems and the uses of such perfume delivery systems are disclosed in USPA 2007/0275866 A1. Such perfume delivery systems include:

I. Polymer Assisted Delivery (PAD): This perfume delivery technology uses polymeric materials to deliver perfume materials. Classical coacervation, water soluble or partly soluble to insoluble charged or neutral polymers, liquid crystals, hot melts, hydrogels, perfumed plastics, microcapsules, nano- and micro-latexes, polymeric film formers, and polymeric absorbents, polymeric adsorbents, etc. are some examples. PAD includes but is not limited to:

a.) Matrix Systems: The fragrance is dissolved or dispersed in a polymer matrix or particle. Perfumes, for example, may be 1) dispersed into the polymer prior to formulating into the product or 2) added separately from the polymer during or after formulation of the product. Diffusion of perfume from the polymer is a common trigger that allows or increases the rate of perfume release from a polymeric matrix system that is deposited or applied to the desired surface (situs), although many other triggers are know that may control perfume release. Absorption and/or adsorption into or onto polymeric particles, films, solutions, and the like are aspects of this technology.

Nano- or micro-particles composed of organic materials (e.g., latexes) are examples. Suitable particles include a wide range of materials including, but not limited to polyacetal, polyacrylate, polyacrylic, polyacrylonitrile, polyamide, polyaryletherketone, polybutadiene, polybutylene, polybutylene terephthalate, polychloroprene, poly ethylene, polyethylene terephthalate, polycyclohexylene dimethylene terephthalate, polycarbonate, polychloroprene, polyhydroxyalkanoate, polyketone, polyester, polyethylene, polyetherimide, polyethersulfone, polyethylenechlorinates, polyimide, polyisoprene, polylactic acid, polymethylpentene, polyphenylene oxide, polyphenylene sulfide, polyphthalamide, polypropylene, polystyrene, polysulfone, polyvinyl acetate, polyvinyl chloride, as well as polymers or copolymers based on acrylonitrile-butadiene, cellulose acetate, ethylene-vinyl acetate, ethylene vinyl alcohol, styrene-butadiene, vinyl acetate-ethylene, and mixtures thereof.

"Standard" systems refer to those that are "pre-loaded" with the intent of keeping the pre-loaded perfume associated with the polymer until the moment or moments of perfume release. Such polymers may also suppress the neat product odor and provide a bloom and/or longevity benefit depending on the rate of perfume release. One challenge with such systems is to achieve the ideal balance between 1) in-product stability (keeping perfume inside carrier until you need it) and 2) timely release (during use or from dry situs). Achieving such stability is particularly important during in-product storage and product aging. This challenge is particularly apparent for aqueous-based, surfactant-containing products, such as heavy duty liquid laundry detergents. Many "Standard" matrix systems available effectively become "Equilibrium" systems when formulated into aqueous-based products. One may select an "Equilibrium" system or a Reservoir system, which has acceptable in-product diffusion stability and available triggers for release (e.g., friction). "Equilibrium" systems are those in which the perfume and polymer may be added separately to the product, and the equilibrium interaction between perfume and polymer leads to a benefit at one or more consumer touch points (versus a free perfume control that has no polymer-assisted delivery technology). The polymer may also be pre-loaded with perfume; however, part or all of the perfume may diffuse during in-product storage reaching an equilibrium that includes having desired perfume raw materials (PRMs) associated with the polymer. The polymer then carries the perfume to the surface, and release is typically via perfume diffusion. The use of such equilibrium system polymers has the potential to decrease the neat product odor intensity of the neat product (usually more so in the case of pre-loaded standard system). Deposition of such polymers may serve to "flatten" the release profile and provide increased longevity. As indicated above, such longevity would be achieved by suppressing the initial intensity and may enable the formulator to use more high impact or low odor detection threshold (ODT) or low Kovats Index (KI) PRMs to achieve FMOT benefits without initial intensity that is too strong or distorted. It is important that perfume release occurs within the time frame of the application to impact the desired consumer touch point or touch points. Suitable micro-particles and micro-latexes as well as methods of making same may be found in USPA 2005/0003980 A1. Matrix systems also include hot melt adhesives and perfume plastics. In addition, hydrophobically modified polysaccharides may be formulated into the perfumed product to increase perfume deposition and/or modify perfume release. All such matrix systems, including for example polysaccharides and nanolatexes may be combined with other PDTs, including other PAD systems such as PAD reservoir systems in the form of a perfume microcapsule (PMC). Polymer Assisted Delivery (PAD) matrix systems may include those described in the following references: US Patent Applications 2004/0110648 A1; 2004/0092414 A1; 2004/0091445 A1 and 2004/0087476 A1; and U.S. Pat. Nos. 6,531,444; 6,024,943; 6,042,792; 6,051,540; 4,540,721 and 4,973,422.

Silicones are also examples of polymers that may be used as PDT, and can provide perfume benefits in a manner similar to the polymer-assisted delivery "matrix system". Such a PDT is referred to as silicone-assisted delivery (SAD). One may pre-load silicones with perfume, or use them as an equilibrium system as described for PAD. Suitable silicones as well as making same may be found in WO 2005/102261; USPA 20050124530A1; USPA 20050143282A1; and WO 2003/015736. Functionalized silicones may also be used as described in USPA 2006/003913 A1. Examples of silicones include polydimethylsiloxane and polyalkyldimethylsiloxanes. Other examples include those with amine functionality, which may be used to provide benefits associated with amine-assisted delivery (AAD) and/or polymer-assisted delivery (PAD) and/or amine-reaction products (ARP). Other such examples may be found in U.S. Pat. No. 4,911,852; USPA 2004/0058845 A1; USPA 2004/0092425 A1 and USPA 2005/0003980 A1.

b.) Reservoir Systems: Reservoir systems are also known as a core-shell type technology, or one in which the fragrance is surrounded by a perfume release controlling membrane, which may serve as a protective shell. The material inside the microcapsule is referred to as the core, internal phase, or fill, whereas the wall is sometimes called a shell, coating, or membrane. Microparticles or pressure sensitive capsules or microcapsules are examples of this technology. Microcapsules of the current invention are formed by a variety of procedures that include, but are not limited to, coating, extrusion, spray-drying, interfacial, in-situ and matrix polymerization. The possible shell materials vary widely in their stability toward water. Among the most stable are polyoxymethyleneurea (PMU)-based materials, which may hold certain PRMs for even long periods of time in aqueous solution (or product). Such systems include but are not limited to urea-formaldehyde and/or melamine-formaldehyde. Gelatin-based microcapsules may be prepared so that they dissolve quickly or slowly in water, depending for example on the degree of cross-linking. Many other capsule wall materials are available and vary in the degree of perfume diffusion stability observed. Without wishing to be bound by theory, the rate of release of perfume from a capsule, for example, once deposited on a surface is typically in reverse order of in-product perfume diffusion stability. As such, urea-formaldehyde and melamine-formaldehyde microcapsules for example, typically require a release mechanism other than, or in addition to, diffusion for release, such as mechanical force (e.g., friction, pressure, shear stress) that serves to break the capsule and increase the rate of perfume (fragrance) release. Other triggers include melting, dissolution, hydrolysis or other chemical reaction, electromagnetic radiation, and the like. The use of pre-loaded microcapsules requires the proper ratio of in-product stability and in-use and/or on-surface (on-situs) release, as well as proper selection of PRMs. Microcapsules that are based on urea-formaldehyde and/or melamine-formaldehyde are relatively stable, especially in near neutral aqueous-based solutions. These materials may require a friction trigger which may not be applicable to all product applications. Other microcapsule materials (e.g., gelatin) may be unstable in aqueous-based products and may even provide reduced benefit (versus free perfume control) when in-product aged. Scratch and sniff technologies are yet another example of PAD. Perfume microcapsules (PMC) may include those described in the following references: US Patent Applications: 2003/0125222 A1; 2003/215417 A1; 2003/216488 A1; 2003/158344 A1; 2003/165692 A1; 2004/071742 A1; 2004/071746 A1; 2004/072719 A1; 2004/072720 A1; 2006/0039934 A1; 2003/203829 A1; 2003/195133 A1; 2004/087477 A1; 2004/0106536 A1; and U.S. Pat. Nos. 6,645,479 B1; 6,200,949 B1; 4,882,220; 4,917,920; 4,514,461; 6,106,875 and 4,234,627, 3,594,328 and U.S. RE 32713.

II. Molecule-Assisted Delivery (MAD): Non-polymer materials or molecules may also serve to improve the delivery of perfume. Without wishing to be bound by theory, perfume may non-covalently interact with organic materials, resulting in altered deposition and/or release. Non-limiting examples of such organic materials include but are not limited to hydrophobic materials such as organic oils, waxes, mineral oils, petrolatum, fatty acids or esters, sugars, surfactants, liposomes and even other perfume raw material (perfume oils), as well as natural oils, including body and/or other soils. Perfume fixatives are yet another example. In one aspect, non-polymeric materials or molecules have a CLogP greater than about 2. Molecule-Assisted Delivery (MAD) may also include those described in U.S. Pat. No. 7,119,060 and U.S. Pat. No. 5,506,201.

III. Fiber-Assisted Delivery (FAD): The choice or use of a situs itself may serve to improve the delivery of perfume. In fact, the situs itself may be a perfume delivery technology. For example, different fabric types such as cotton or polyester will have different properties with respect to ability to attract and/or retain and/or release perfume. The amount of perfume deposited on or in fibers may be altered by the choice of fiber, and also by the history or treatment of the fiber, as well as by any fiber coatings or treatments. Fibers may be woven and non-woven as well as natural or synthetic. Natural fibers include those produced by plants, animals, and geological processes, and include but are not limited to cellulose materials such as cotton, linen, hemp jute, flax, ramie, and sisal, and fibers used to manufacture paper and cloth. Fiber-Assisted Delivery may consist of the use of wood fiber, such as thermomechanical pulp and bleached or unbleached kraft or sulfite pulps. Animal fibers consist largely of particular proteins, such as silk, sinew, catgut and hair (including wool). Polymer fibers based on synthetic chemicals include but are not limited to polyamide nylon, PET or PBT polyester, phenol-formaldehyde (PF), polyvinyl alcohol fiber (PVOH), polyvinyl chloride fiber (PVC), polyolefins (PP and PE), and acrylic polymers. All such fibers may be pre-loaded with a perfume, and then added to a product that may or may not contain free perfume and/or one or more perfume delivery technologies. In one aspect, the fibers may be added to a product prior to being loaded with a perfume, and then loaded with a perfume by adding a perfume that may diffuse into the fiber, to the product. Without wishing to be bound by theory, the perfume may absorb onto or be adsorbed into the fiber, for example, during product storage, and then be released at one or more moments of truth or consumer touch points.

IV. Amine Assisted Delivery (AAD): The amine-assisted delivery technology approach utilizes materials that contain an amine group to increase perfume deposition or modify perfume release during product use. There is no requirement in this approach to pre-complex or pre-react the perfume raw material(s) and amine prior to addition to the product. In one aspect, amine-containing AAD materials suitable for use herein may be non-aromatic; for example, polyalkylimine, such as polyethyleneimine (PEI), or polyvinylamine (PVAm), or aromatic, for example, anthranilates. Such materials may also be polymeric or non-polymeric. In one aspect, such materials contain at least one primary amine. This technology will allow increased longevity and controlled release also of low ODT perfume notes (e.g., aldehydes, ketones, enones) via amine functionality, and delivery of other PRMs, without being bound by theory, via polymer-assisted delivery for polymeric amines. Without technology, volatile top notes can be lost too quickly, leaving a higher ratio of middle and base notes to top notes. The use of a polymeric amine allows higher levels of top notes and other PRMS to be used to obtain freshness longevity without causing neat product odor to be more intense than desired, or allows top notes and other PRMs to be used more efficiently. In one aspect, AAD systems are effective at delivering PRMs at pH greater than about neutral. Without wishing to be bound by theory, conditions in which more of the amines of the AAD system are deprotonated may result in an increased affinity of the deprotonated amines for PRMs such as aldehydes and ketones, including unsaturated ketones and enones such as damascone. In another aspect, polymeric amines are effective at delivering PRMs at pH less than about neutral. Without wishing to be bound by theory, conditions in which more of the amines of the AAD system are protonated may result in a decreased affinity of the protonated amines for PRMs such as aldehydes and ketones, and a strong affinity of the polymer framework for a broad range of PRMs. In such an aspect, polymer-assisted delivery may be delivering more of the perfume benefit; such systems are a subspecies of AAD and may be referred to as Amine-Polymer-Assisted Delivery or APAD. In some cases when the APAD is employed in a composition that has a pH of less than seven, such APAD systems may also be considered Polymer-Assisted Delivery (PAD). In yet another aspect, AAD and PAD systems may interact with other materials, such as anionic surfactants or polymers to form coacervate and/or coacervates-like systems. In another aspect, a material that contains a heteroatom other than nitrogen, for example sulfur, phosphorus or selenium, may be used as an alternative to amine compounds. In yet another aspect, the aforementioned alternative compounds can be used in combination with amine compounds. In yet another aspect, a single molecule may comprise an amine moiety and one or more of the alternative heteroatom moieties, for example, thiols, phosphines and selenols. Suitable AAD systems as well as methods of making same may be found in US Patent Applications 2005/0003980 A1; 2003/0199422 A1; 2003/0036489 A1; 2004/0220074 A1 and U.S. Pat. No. 6,103,678.

V. Cyclodextrin Delivery System (CD): This technology approach uses a cyclic oligosaccharide or cyclodextrin to improve the delivery of perfume. Typically a perfume and cyclodextrin (CD) complex is formed. Such complexes may be preformed, formed in-situ, or formed on or in the situs. Without wishing to be bound by theory, loss of water may serve to shift the equilibrium toward the CD-Perfume complex, especially if other adjunct ingredients (e.g., surfactant) are not present at high concentration to compete with the perfume for the cyclodextrin cavity. A bloom benefit may be achieved if water exposure or an increase in moisture content occurs at a later time point. In addition, cyclodextrin allows the perfume formulator increased flexibility in selection of PRMs. Cyclodextrin may be pre-loaded with perfume or added separately from perfume to obtain the desired perfume stability, deposition or release benefit. Suitable CDs as well as methods of making same may be found in USPA 2005/0003980 A1 and 2006/0263313 A1 and U.S. Pat. Nos. 5,552,378; 3,812,011; 4,317,881; 4,418,144 and 4,378,923.

VI. Starch Encapsulated Accord (SEA): The use of a starch encapsulated accord (SEA) technology allows one to modify the properties of the perfume, for example, by converting a liquid perfume into a solid by adding ingredients such as starch. The benefit includes increased perfume retention during product storage, especially under non-aqueous conditions. Upon exposure to moisture, a perfume bloom may be triggered. Benefits at other moments of truth may also be achieved because the starch allows the product formulator to select PRMs or PRM concentrations that normally cannot be used without the presence of SEA. Another technology example includes the use of other organic and inorganic materials, such as silica to convert perfume from liquid to solid. Suitable SEAs as well as methods of making same may be found in USPA 2005/0003980 A1 and U.S. Pat. No. 6,458,754 B1.

VII. Inorganic Carrier Delivery System (ZIC): This technology relates to the use of porous zeolites or other inorganic materials to deliver perfumes. Perfume-loaded zeolite may be used with or without adjunct ingredients used for example to coat the perfume-loaded zeolite (PLZ) to change its perfume release properties during product storage or during use or from the dry situs. Suitable zeolite and inorganic carriers as well as methods of making same may be found in USPA 2005/0003980 A1 and U.S. Pat. Nos. 5,858,959; 6,245,732 B1; 6,048,830 and 4,539,135. Silica is another form of ZIC. Another example of a suitable inorganic carrier includes inorganic tubules, where the perfume or other active material is contained within the lumen of the nano- or micro-tubules. Preferably, the perfume-loaded inorganic tubule (or Perfume-Loaded Tubule or PLT) is a mineral nano- or micro-tubule, such as halloysite or mixtures of halloysite with other inorganic materials, including other clays. The PLT technology may also comprise additional ingredients on the inside and/or outside of the tubule for the purpose of improving in-product diffusion stability, deposition on the desired situs or for controlling the release rate of the loaded perfume. Monomeric and/or polymeric materials, including starch encapsulation, may be used to coat, plug, cap, or otherwise encapsulate the PLT. Suitable PLT systems as well as methods of making same may be found in U.S. Pat. No. 5,651,976.

VIII. Pro-Perfume (PP): This technology refers to perfume technologies that result from the reaction of perfume materials with other substrates or chemicals to form materials that have a covalent bond between one or more PRMs and one or more carriers. The PRM is converted into a new material called a pro-PRM (i.e., pro-perfume), which then may release the original PRM upon exposure to a trigger such as water or light. Pro-perfumes may provide enhanced perfume delivery properties such as increased perfume deposition, longevity, stability, retention, and the like. Pro-perfumes include those that are monomeric (non-polymeric) or polymeric, and may be pre-formed or may be formed in-situ under equilibrium conditions, such as those that may be present during in-product storage or on the wet or dry situs. Nonlimiting examples of pro-perfumes include Michael adducts (e.g., beta-amino ketones), aromatic or non-aromatic imines (Schiffs Bases), oxazolidines, beta-keto esters, and orthoesters. Another aspect includes compounds comprising one or more beta-oxy or beta-thio carbonyl moieties capable of releasing a PRM, for example, an alpha, beta-unsaturated ketone, aldehyde or carboxylic ester. The typical trigger for perfume release is exposure to water; although other triggers may include enzymes, heat, light, pH change, autoxidation, a shift of equilibrium, change in concentration or ionic strength and others. For aqueous-based products, light-triggered pro-perfumes are particularly suited. Such photo-pro-perfumes (PPPs) include but are not limited to those that release coumarin derivatives and perfumes and/or pro-perfumes upon being triggered. The released pro-perfume may release one or more PRMs by means of any of the above mentioned triggers. In one aspect, the photo-pro-perfume releases a nitrogen-based pro-perfume when exposed to a light and/or moisture trigger. In another aspect, the nitrogen-based pro-perfume, released from the photo-pro-perfume, releases one or more PRMs selected, for example, from aldehydes, ketones (including enones) and alcohols. In still another aspect, the PPP releases a dihydroxy coumarin derivative. The light-triggered pro-perfume may also be an ester that releases a coumarin derivative and a perfume alcohol. In one aspect the pro-perfume is a dimethoxybenzoin derivative as described in USPA 2006/0020459 A1. In another aspect the pro-perfume is a 3', 5'-dimethoxybenzoin (DMB) derivative that releases an alcohol upon exposure to electromagnetic radiation. In yet another aspect, the pro-perfume releases one or more low ODT PRMs, including tertiary alcohols such as linalool, tetrahydrolinalool, or dihydromyrcenol. Suitable pro-perfumes and methods of making same can be found in U.S. Pat. Nos. 7,018,978 B2; 6,987,084 B2; 6,956,013 B2; 6,861,402 B1; 6,544,945 B1; 6,093,691; 6,277,796 B1; 6,165,953; 6,316,397 B1; 6,437,150 B1; 6,479,682 B1; 6,096,918; 6,218,355 B1; 6,133,228; 6,147,037; 7,109,153 B2; 7,071,151 B2; 6,987,084 B2; 6,610,646 B2 and 5,958,870, as well as can be found in USPA 2005/0003980 A1 and USPA 2006/0223726 A1.

a.) Amine Reaction Product (ARP): For purposes of the present application, ARP is a subclass or species of PP. One may also use "reactive" polymeric amines in which the amine functionality is pre-reacted with one or more PRMs to form an amine reaction product (ARP). Typically the reactive amines are primary and/or secondary amines, and may be part of a polymer or a monomer (non-polymer). Such ARPs may also be mixed with additional PRMs to provide benefits of polymer-assisted delivery and/or amine-assisted delivery. Nonlimiting examples of polymeric amines include polymers based on polyalkylimines, such as polyethyleneimine (PEI), or polyvinylamine (PVAm). Nonlimiting examples of monomeric (non-polymeric) amines include hydroxylamines, such as 2-aminoethanol and its alkyl substituted derivatives, and aromatic amines such as anthranilates. The ARPs may be premixed with perfume or added separately in leave-on or rinse-off applications. In another aspect, a material that contains a heteroatom other than nitrogen, for example oxygen, sulfur, phosphorus or selenium, may be used as an alternative to amine compounds. In yet another aspect, the aforementioned alternative compounds can be used in combination with amine compounds. In yet another aspect, a single molecule may comprise an amine moiety and one or more of the alternative heteroatom moieties, for example, thiols, phosphines and selenols. The benefit may include improved delivery of perfume as well as controlled perfume release. Suitable ARPs as well as methods of making same can be found in USPA 2005/0003980 A1 and U.S. Pat. No. 6,413,920 B1.

In one aspect, the perfumes comprising the replacement materials disclosed in Table 1 and stereoisomers thereof are suitable for use, in perfume delivery systems at levels, based on total perfume delivery system weight, of from 0.001% to about 50%, from 0.005% to 30%, from 0.01% to about 10%, from 0.025% to about 5%, or even from 0.025% to about 1%.

In one aspect, the perfume delivery systems disclosed herein are suitable for use in consumer products, cleaning and treatment compositions and fabric and hard surface cleaning and/or treatment compositions, detergents, and highly compacted consumer products, including highly compacted fabric and hard surface cleaning and/or treatment compositions, for example highly compacted detergents that may be solids or fluids, at levels, based on total consumer product weight, from about 0.001% to about 20%, from about 0.01% to about 10%, from about 0.05% to about 5%, from about 0.1% to about 0.5%.

In one aspect, the amount of Table 1 PRMs, based on the total microcapsules and/or nanocapsules (Polymer Assisted Delivery (PAD) Reservoir System) weight, may be from about 0.1% to about 99%, from 25% to about 95%, from 30 to about 90%, from 45% to about 90%, from 65% to about 90%.

In one aspect, the amount of total perfume based on total weight of starch encapsulates and starch agglomerates (Starch Encapsulated Accord (SEA)) ranges from 0.1% to about 99%, from 25% to about 95%, from 30 to about 90%, from 45% to about 90%, from 65% to about 90%. In one aspect, the perfumes comprising the replacement materials disclosed in Table 1 and stereoisomers thereof are suitable for use, in such starch encapsulates and starch agglomerates. Such PRMs and stereoisomers thereof may be used in combination in such starch encapsulates and starch agglomerates.

In one aspect, the amount of total perfume based on total weight of [cyclodextrin-perfume] complexes (Cyclodextrin (CD)) ranges from 0.1% to about 99%, from 2.5% to about 75%, from 5% to about 60%, from 5% to about 50%, from 5% to about 25%. In one aspect, the perfumes comprising the replacement materials disclosed in Table 1 and stereoisomers thereof are suitable for use in such [cyclodextrin-perfume] complexes. Such PRMs and stereoisomers thereof may be used in combination in such [cyclodextrin-perfume] complexes.

In one aspect, the amount of total perfume based on total weight of Polymer Assisted Delivery (PAD) Matrix Systems (including Silicones) ranges from 0.1% to about 99%, from 2.5% to about 75%, from 5% to about 60%, from 5% to about 50%, from 5% to about 25%. In one aspect, the amount of total perfume based on total weight of a hot melt perfume delivery system/perfume loaded plastic Matrix System and ranges from 1% to about 99%, from 2.5% to about 75%, from 5% to about 60%, from 5% to about 50%, from 10% to about 50%. In one aspect, the perfumes comprising the replacement materials disclosed in Table 1 and stereoisomers thereof, are suitable for use, in such Polymer Assisted Delivery (PAD) Matrix Systems, including hot melt perfume delivery system/perfume loaded plastic Matrix Systems. Such PRMs and stereoisomers thereof may be used in combination in such Polymer Assisted Delivery (PAD) Matrix Systems (including hot melt perfume delivery system/perfume loaded plastic Matrix Systems).

In one aspect, the amount of total perfume based on total weight of Amine Assisted Delivery (AAD) (including Aminosilicones) ranges from 1% to about 99%, from 2.5% to about 75%, from 5% to about 60%, from 5% to about 50%, from 5% to about 25%. In one aspect, the perfumes comprising the replacement materials disclosed in Table 1 and stereoisomers thereof are suitable for use, in such Amine Assisted Delivery (AAD) systems.

In one aspect, the amount of total perfume based on total weight of Pro-Perfume (PP) Amine Reaction Product (ARP) system ranges from 0.1% to about 99%, from about 1% to about 99%, from 5% to about 90%, from 10% to about 75%, from 20% to about 75%, from 25% to about 60%. In one aspect, the perfumes comprising the replacement materials disclosed in Table 1 and stereoisomers thereof are suitable for use, in such Pro-Perfume (PP) Amine Reaction Product (ARP) systems The perfume delivery technologies also known as perfume delivery systems that are disclosed in the present specification may be used in any combination in any type of consumer product, cleaning and/or treatment composition, fabric and hard surface cleaning and/or treatment composition, detergent, and highly compact detergent.

Adjunct Materials

For the purposes of the present invention, the non-limiting list of adjuncts illustrated hereinafter are suitable for use in the instant compositions and may be desirably incorporated in certain embodiments of the invention, for example to assist or enhance performance, for treatment of the substrate to be cleaned, or to modify the aesthetics of the composition as is the case with perfumes, colorants, dyes or the like. It is understood that such adjuncts are in addition to the components that are supplied via Applicants' perfumes and/or perfume systems. The precise nature of these additional components, and levels of incorporation thereof, will depend on the physical form of the composition and the nature of the operation for which it is to be used. Suitable adjunct materials include, but are not limited to, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

Each adjunct ingredients is not essential to Applicants' compositions. Thus, certain embodiments of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, structure elasticizing agents, fabric softeners, carriers, hydrotropes, processing aids and/or pigments. However, when one or more adjuncts are present, such one or more adjuncts may be present as detailed below:

Surfactants—The compositions according to the present invention can comprise a surfactant or surfactant system wherein the surfactant can be selected from nonionic and/or anionic and/or cationic surfactants and/or ampholytic and/or zwitterionic and/or semi-polar nonionic surfactants. The surfactant is typically present at a level of from about 0.1%, from about 1%, or even from about 5% by weight of the cleaning compositions to about 99.9%, to about 80%, to about 35%, or even to about 30% by weight of the cleaning compositions.

Builders—The compositions of the present invention can comprise one or more detergent builders or builder systems. When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders polycarboxylate compounds. ether hydroxypolycarboxylates, copolymers of maleic anhydride with ethylene or vinyl methyl ether, 1,3,5-trihydroxybenzene-2,4,6-trisulphonic acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The compositions herein may also optionally contain one or more copper, iron and/or manganese chelating agents. If utilized, chelating agents will generally comprise from about 0.1% by weight of the compositions herein to about 15%, or even from about 3.0% to about 15% by weight of the compositions herein.

Dye Transfer Inhibiting Agents—The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Dispersants—The compositions of the present invention can also contain dispersants. Suitable water-soluble organic materials are the homo- or co-polymeric acids or their salts, in which the polycarboxylic acid may comprise at least two carboxyl radicals separated from each other by not more than two carbon atoms.

Enzymes—The compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

Enzyme Stabilizers—Enzymes for use in compositions, for example, detergents can be stabilized by various techniques. The enzymes employed herein can be stabilized by the presence of water-soluble sources of calcium and/or magnesium ions in the finished compositions that provide such ions to the enzymes.

Catalytic Metal Complexes—Applicants' compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methyl-enephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936 and 5,595,967. Such cobalt catalysts are readily prepared by known procedures, such as taught for example in U.S. Pat. Nos. 5,597,936, and 5,595,967.

Compositions herein may also suitably include a transition metal complex of a macropolycyclic rigid ligand—abbreviated as "MRL". As a practical matter, and not by way of limitation, the compositions and cleaning processes herein can be adjusted to provide on the order of at least one part per hundred million of the benefit agent MRL species in the aqueous washing medium, and may provide from about 0.005 ppm to about 25 ppm, from about 0.05 ppm to about 10 ppm, or even from about 0.1 ppm to about 5 ppm, of the MRL in the wash liquor.

Suitable transition-metals in the instant transition-metal bleach catalyst include manganese, iron and chromium. Suitable MRL's herein are a special type of ultra-rigid ligand that is cross-bridged such as 5,12-diethyl-1,5,8,12-tetraazabicyclo[6.6.2]hexa-decane.

Suitable transition metal MRLs are readily prepared by known procedures, such as taught for example in WO 00/32601, and U.S. Pat. No. 6,225,464.

Method of Use

Certain of the consumer products disclosed herein can be used to clean or treat a situs inter alia a surface or fabric. Typically at least a portion of the situs is contacted with an embodiment of Applicants' composition, in neat form or diluted in a liquor, for example, a wash liquor and then the situs may be optionally washed and/or rinsed. In one aspect, a situs is optionally washed and/or rinsed, contacted with a particle according to the present invention or composition comprising said particle and then optionally washed and/or rinsed. For purposes of the present invention, washing includes but is not limited to, scrubbing, and mechanical agitation. The fabric may comprise most any fabric capable of being laundered or treated in normal consumer use conditions. Liquors that may comprise the disclosed compositions may have a pH of from about 3 to about 11.5. Such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1.

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Example 1 p-tert.Butyl-alpha-methyldihydrocinnamic aldehyde Replacement Cocktails and Perfume Compositions Comprising Such Replacement Cocktails

TABLE A

Representative cocktails to replace p-tert.Butyl-alpha-methyldihydrocinnamic aldehyde expressed in replacement ratios

| No. | A | B | C | D | E | F | G | H | I | J | K | L |
|---|---|---|---|---|---|---|---|---|---|---|---|---|
| 1 | — | — | — | — | — | — | 0.217 | 0.100 | — | — | — | |
| 2 | — | — | — | — | — | — | — | — | — | — | 0.020 | |
| 3 | — | — | — | — | — | 0.200 | 0.185 | 0.158 | — | — | — | |
| 4 | — | — | — | — | — | 0.025 | — | — | — | 0.015 | — | 0.075 |
| 5 | — | — | — | — | — | — | 0.010 | 0.010 | — | — | — | |
| 6 | — | — | — | — | — | — | — | — | — | — | — | |
| 8 | — | — | — | — | — | — | 0.160 | 0.100 | — | — | — | |
| 9 | — | — | — | — | — | 0.050 | — | 0.015 | — | 0.010 | — | |
| 13 | — | — | 0.030 | 0.030 | 0.030 | 0.170 | — | — | — | 0.150 | — | 0.075 |
| 14 | 0.015 | — | — | — | — | — | 0.015 | 0.010 | — | — | — | |
| 16 | 0.003 | — | — | — | — | — | 0.003 | 0.008 | — | — | — | |
| 17 | — | 0.078 | — | — | — | — | — | — | — | 0.010 | — | |
| 18 | — | — | 0.970 | — | — | — | — | — | — | — | — | |
| 20 | — | — | — | — | 0.970 | 0.199 | 0.210 | 0.156 | — | 0.249 | — | |
| 22 | — | — | — | 0.970 | — | — | — | — | — | — | — | |
| 23 | — | — | — | — | — | 0.125 | — | 0.150 | — | — | 0.100 | |
| 24 | — | — | — | — | — | 0.125 | — | — | — | 0.140 | — | |
| 26 | — | — | — | — | — | — | — | 0.040 | 0.150 | — | 0.010 | |
| 27 | — | — | — | — | — | — | — | — | 0.100 | — | — | |
| 28 | — | — | — | — | — | 0.005 | — | 0.003 | — | 0.010 | 0.004 | |
| 34 | — | — | — | — | — | 0.100 | — | 0.030 | — | — | — | |
| 38 | | | | | | | | | | | | 0.850 |
| 39 | — | — | — | — | — | — | — | — | 0.500 | — | — | |
| 42 | — | — | — | — | — | — | — | — | 0.250 | — | — | |
| 43 | — | — | — | — | — | — | — | 0.050 | — | — | — | |
| 44 | — | — | — | — | — | — | — | — | — | 0.100 | — | |
| 45 | — | — | — | — | — | 0.001 | — | — | — | — | — | |
| 46 | — | — | — | — | — | — | — | — | — | — | 0.003 | |
| 56 | — | — | — | — | — | — | 0.200 | 0.020 | — | 0.200 | — | |
| 66 | — | — | — | — | — | — | — | 0.150 | — | — | — | |
| 71 | — | — | — | — | — | — | — | — | — | — | 0.015 | |
| 76 | — | — | — | — | — | — | — | — | — | 0.100 | — | |
| 77 | — | 0.002 | — | — | — | — | — | — | — | — | 0.848 | |
| 80 | — | — | — | — | — | — | — | — | — | 0.005 | — | |
| 84 | — | — | — | — | — | — | — | — | — | 0.010 | — | |
| 87 | — | — | — | — | — | — | — | — | — | 0.001 | — | |
| 93 | — | — | — | — | — | — | — | — | — | — | — | |
| O.S. * | 0.982 | 0.920 | — | — | — | — | — | — | — | — | — | — |
| Total | 1.0000 | 1.0000 | 1.0000 | 1.0000 | 1.0000 | 1.0000 | 1.0000 | 1.0000 | 1.0000 | 1.0000 | 1.0000 | 1.0000 |

OS *: Any odorless solvent such as Dipropylene glycol (CAS 25265-71-8), 1,2,3-Propanetricarboxylic acid, 2-hydroxy-, triethyl ester (CAS77-93-0), 1,2-Benzenedicarboxylic acid, diethyl ester (CAS 84-66-2) etc.

TABLE B

Applications of p-tert.Butyl-alpha-methyldihydrocinnamic aldehyde replacement cocktails in finished perfumes

| CAS | Water Floral Perfume Chemical Name | Original Perfume % | Example I % | Example II % | Example III % | Example IV % | Example V % |
|---|---|---|---|---|---|---|---|
| 28940-11-6 | 2H-1,5-Benzodioxepin-3(4H)-one, 7-methyl- | 1.20 | 1.20 | 1.20 | 1.20 | 1.20 | 1.20 |
| 106-22-9 | 6-Octen-1-ol, 3,7-dimethyl- | 4.00 | 4.00 | 4.00 | 4.00 | 4.00 | 4.00 |
| 17283-81-7 | 4-(2,6,6-Trimethyl-1-cyclohexe-1-nyl)butan-2-one | 6.50 | 6.50 | 6.50 | 6.50 | 6.50 | 6.50 |
| 1205-17-0 | 1,3-Benzodioxole-5-propanal, .alpha.-methyl- | 3.50 | 3.50 | 3.50 | 3.50 | 3.50 | 3.50 |
| 1222-05-5 | 1,3,4,6,7,8-hexahydro-4,6,6,7,8,8-hexamethylcyclopenta-gamma-2-benzopyran (50 IPM) | 28.00 | 28.00 | 28.00 | 28.00 | 28.00 | 28.00 |

TABLE B-continued

Applications of p-tert.Butyl-alpha-methyldihydrocinnamic aldehyde replacement cocktails in finished perfumes

| CAS | Water Floral Perfume Chemical Name | Original Perfume % | Example I % | Example II % | Example III % | Example IV % | Example V % |
|---|---|---|---|---|---|---|---|
| 18096-62-3 | Indeno[1,2-d]-1,3-dioxin, 4,4a,5,9b-tetrahydro- | 0.05 | 0.05 | 0.05 | 0.05 | 0.05 | 0.05 |
| 54464-57-2 | Ethanone, 1-(1,2,3,4,5,6,7,8-octahydro-2,3,8,8-tetramethyl-2-naphthalenyl)- | 19.00 | 19.00 | 19.00 | 19.00 | 19.00 | 19.00 |
| 31906-04-4 | 3-Cyclohexene-1-carboxaldehyde, 4-(4-hydroxy-4-methylpentyl)- | 3.00 | 3.00 | 3.00 | 3.00 | 3.00 | 3.00 |
| 24851-98-7 | Cyclopentaneacetic acid, 3-oxo-2-pentyl-, methyl ester | 18.00 | 18.00 | 18.00 | 18.00 | 18.00 | 18.00 |
| 65996-98-7 | Terpenes and Terpenoids, limonene fraction | 1.50 | 1.50 | 1.50 | 1.50 | 1.50 | 1.50 |
| 122-78-1 | Benzeneacetaldehyde | 0.25 | 0.25 | 0.25 | 0.25 | 0.25 | 0.25 |
| 18479-57-7 | 2-Octanol, 2,6-dimethyl- | 5.00 | 5.00 | 5.00 | 5.00 | 5.00 | 5.00 |
| 80-54-6 | p-tert.Butyl-alpha-methyldihydrocinnamic aldehyde | 10.00 | — | — | — | — | — |
| Mixture | Cocktail A From Table A | — | 10.00 | — | — | — | — |
| Mixture | Cocktail B From Table A | — | — | 10.00 | — | — | — |
| Mixture | Cocktail C From Table A | — | — | — | 10.00 | — | — |
| Mixture | Cocktail D From Table A | — | — | — | — | 10.00 | — |
| Mixture | Cocktail E From Table A | — | — | — | — | — | 10.00 |
| | Total | 100.00 | 100.00 | 100.00 | 100.00 | 100.00 | 100.00 |

TABLE C

Finished perfumes wherein p-tert.Butyl-alpha-methyldihydrocinnamic aldehyde is replaced by a single Table 1 Material

| CAS | Water Floral Perfume Chemical Name | Original Perfume % | Example VI % | Example VII % | Example VIII % | Example IX % | Example X % |
|---|---|---|---|---|---|---|---|
| 28940-11-6 | 2H-1,5-Benzodioxepin-3(4H)-one, 7-methyl- | 1.20 | 1.20 | 1.20 | 1.20 | 1.20 | 1.20 |
| 106-22-9 | 6-Octen-1-ol, 3,7-dimethyl- | 4.00 | 4.00 | 4.00 | 4.00 | 4.00 | 4.00 |
| 17283-81-7 | 4-(2,6,6-Trimethyl-1-cyclohexe-1-nyl)butan-2-one | 6.50 | 6.50 | 6.50 | 6.50 | 6.50 | 6.50 |
| 1205-17-0 | 1,3-Benzodioxole-5-propanal, .alpha.-methyl- | 3.50 | 3.50 | 3.50 | 3.50 | 3.50 | 3.50 |
| 1222-05-5 | 1,3,4,6,7,8-hexahydro-4,6,6,7,8,8-hexamethylcyclopenta-gamma-2-benzopyran (50 IPM) | 28.00 | 28.00 | 28.00 | 28.00 | 28.00 | 28.00 |
| 18096-62-3 | Indeno[1,2-d]-1,3-dioxin, 4,4a,5,9b-tetrahydro- | 0.05 | 0.05 | 0.05 | 0.05 | 0.05 | 0.05 |
| 54464-57-2 | Ethanone, 1-(1,2,3,4,5,6,7,8-octahydro-2,3,8,8-tetramethyl-2-naphthalenyl)- | 19.00 | 19.00 | 19.00 | 19.00 | 19.00 | 19.00 |
| 31906-04-4 | 3-Cyclohexene-1-carboxaldehyde, 4-(4-hydroxy-4-methylpentyl)- | 3.00 | 3.00 | 3.00 | 3.00 | 3.00 | 3.00 |
| 24851-98-7 | Cyclopentaneacetic acid, 3-oxo-2-pentyl-, methyl ester | 18.00 | 18.00 | 18.00 | 18.00 | 18.00 | 18.00 |
| 65996-98-7 | Terpenes and Terpenoids, limonene fraction | 1.50 | 1.50 | 1.50 | 1.50 | 1.50 | 1.50 |
| 122-78-1 | Benzeneacetaldehyde | 0.25 | 0.25 | 0.25 | 0.25 | 0.25 | 0.25 |
| 18479-57-7 | 2-Octanol, 2,6-dimethyl- | 5.00 | 5.00 | 5.00 | 5.00 | 5.00 | 5.00 |
| 80-54-6 | p-tert.Butyl-alpha-methyldihydrocinnamic aldehyde | 10.00 | — | — | — | — | — |
| 18127-01-0 | 4-(1,1-Dimethylethyl)benzenepropanal | — | 1.0 | — | — | — | — |
| 7775-00-0 | Propanal, 3-(4-isopropylphenyl)- | — | — | 0.75 | — | — | — |

TABLE C-continued

| Finished perfumes wherein p-tert.Butyl-alpha-methyldihydrocinnamic aldehyde is replaced by a single Table 1 Material | | | | | | | |
|---|---|---|---|---|---|---|---|
| CAS | Water Floral Perfume Chemical Name | Original Perfume % | Example VI % | Example VII % | Example VIII % | Example IX % | Example X % |
| 125109-85-5 | Benzenepropanal, .beta.-methyl-3-(1-methylethyl)- | — | — | — | 1.0 | — | — |
| 6658-48-6 | 2-Methyl-3-(4-(2-methylpropyl)phenyl)propanal | — | — | — | — | 10.00 | — |
| 31906-04-4 | 3-Cyclohexene-1-carboxaldehyde, 4-(4-hydroxy-4-methylpentyl)- | — | — | — | — | — | 10.00 |
| | OS* | | 9.00 | 9.25 | 9.00 | | |
| | Total | 100.00 | 100.00 | 100.00 | 100.00 | 100.00 | 100.00 |

OS*: Any odorless solvent such as Dipropylene glycol (CAS 25265-71-8), 1,2,3- Propanetricarboxylic acid, 2-hydroxy-, triethyl ester (CAS77-93-0), 1,2-Benzenedicarboxylic acid, diethyl ester (CAS 84-66-2) etc.

Example 2

Preformed Amine Reaction Product

The following ingredients are weighted off in a glass vial:

50% of the perfume material comprising one or more Table 1 PRMs

50% of Lupasol WF (CAS#09002-98-6) from BASF, is put at 60° C. in warm water bath for 1 hour before use. Mixing of the two ingredients is done by using the Ultra-Turrax T25 Basic equipment (from IKA) during 5 minutes. When the mixing is finished the sample is put in a warm water bath at 60° C. for ±12 hours. A homogenous, viscous material is obtained. In the same way as described above different ratios between the components can be used:

| | Weight % | | | | |
|---|---|---|---|---|---|
| Perfume Material | 40 | 50 | 60 | 70 | 80 |
| Lupasol WF | 60 | 50 | 40 | 30 | 20 |

Example 3

84 wt % Core/16 wt % Wall Melamine Formaldehyde (MF) Capsule (PAD Reservoir System 25 grams of butyl acrylate-acrylic acid copolymer emulsifier (Colloid C351, 25% solids, pka 4.5-4.7, (Kemira Chemicals, Inc. Kennesaw, Ga. U.S.A.) is dissolved and mixed in 200 grams deionized water. The pH of the solution is adjusted to pH of 4.0 with sodium hydroxide solution. 8 grams of partially methylated methylol melamine resin (Cymel 385, 80% solids, (Cytec Industries West Paterson, N.J., U.S.A.)) is added to the emulsifier solution. 200 grams of perfume oil comprising one or more Table 1 PRMs is added to the previous mixture under mechanical agitation and the temperature is raised to 50° C. After mixing at higher speed until a stable emulsion is obtained, the second solution and 4 grams of sodium sulfate salt are added to the emulsion. This second solution contains 10 grams of butyl acrylate-acrylic acid copolymer emulsifier (Colloid C351, 25% solids, pka 4.5-4.7, Kemira), 120 grams of distilled water, sodium hydroxide solution to adjust pH to 4.8, 25 grams of partially methylated methylol melamine resin (Cymel 385, 80% solids, Cytec). This mixture is heated to 70° C. and maintained overnight with continuous stirring to complete the encapsulation process. 23 grams of acetoacetamide (Sigma-Aldrich, Saint Louis, Mo., U.S.A.) is added to the suspension. An average capsule size of 30 um is obtained as analyzed by a Model 780 Accusizer.

Example 4

Process of Making a Polymer Assisted Delivery (PAD) Matrix System

A mixture comprising 50% of a perfume composition comprising one or more Table 1 PRMs, 40% of carboxyl-terminated Hycar® 1300X18 (CAS#0068891-50-9) from Noveon, (put at 60° C. in warm water bath for 1 hour before mixing) and 10% of Lupasol® WF(CAS#09002-98-6) from BASF (put at 60° C. in warm water bath for 1 hour before mixing). Mixing is achieved by mixing for five minutes using a Ultra-Turrax T25 Basic equipment (from IKA). After mixing, the mixture is put in a warm water bath at 60° C. for ±12 hours. A homogenous, viscous and sticky material is obtained.

In the same way as described above different ratios between the components can be used:

| | Weight % | | | | |
|---|---|---|---|---|---|
| Perfume composition | 40 | 50 | 60 | 70 | 80 |
| Lupasol ® WF | 12 | 10 | 8 | 6 | 4 |
| Hycar ® CTBN1300X18 | 48 | 40 | 32 | 24 | 16 |

| | Weight % | | | | | | | |
|---|---|---|---|---|---|---|---|---|
| Perfume composition | 50 | 50 | 50 | 50 | 50 | 50 | 50 | 50 |
| Lupasol ® WF | 2.5 | 5 | 7.5 | 10 | 12.5 | 15 | 17.5 | 20 |
| Hycar ® CTBN1300X18 | 47.5 | 45 | 42.5 | 40 | 37.5 | 35 | 32.5 | 30 |

Example 5

Product Formulation—Fabric Softener

Non-limiting examples of product formulations containing PRMs disclosed in the present specification perfume and amines summarized in the following table.

| (% wt) | EXAMPLES | | | | | | | | | |
|---|---|---|---|---|---|---|---|---|---|---|
| | XI | XII | XIII | XIV | XV | XVI | XVII | XVIII | XIX | XX |
| FSA[a] | 14 | 16.47 | 14 | 12 | 12 | 16.47 | — | — | 5 | 5 |
| FSA[b] | | | | | — | | 3.00 | — | — | — |
| FSA[c] | | | | | — | | — | 6.5 | — | — |
| Ethanol | 2.18 | 2.57 | 2.18 | 1.95 | 1.95 | 2.57 | — | — | 0.81 | 0.81 |
| Isopropyl Alcohol | — | — | — | — | — | — | 0.33 | 1.22 | — | — |
| Starch[d] | 1.25 | 1.47 | 2.00 | 1.25 | — | 2.30 | 0.5 | 0.70 | 0.71 | 0.42 |
| Amine* | 0.6 | 0.75 | 0.6 | 0.75 | 0.37 | 0.60 | 0.37 | 0.6 | 0.37 | 0.37 |
| Perfume X[e] | 0.40 | 0.13 | 0.065 | 0.25 | 0.03 | 0.030 | 0.030 | 0.065 | 0.03 | 0.03 |
| Phase Stabilizing Polymer[f] | 0.21 | 0.25 | 0.21 | 0.21 | 0.14 | — | — | 0.14 | — | — |
| Suds Suppressor[g] | — | — | — | — | — | — | — | 0.1 | — | — |
| Calcium Chloride | 0.15 | 0.176 | 0.15 | 0.15 | 0.30 | 0.176 | — | 0.1-0.15 | — | — |
| DTPA[h] | 0.017 | 0.017 | 0.017 | 0.017 | 0.007 | 0.007 | 0.20 | — | 0.002 | 0.002 |
| Preservative (ppm)[i,j] | 5 | 5 | 5 | 5 | 5 | 5 | — | 250[j] | 5 | 5 |
| Antifoam[k] | 0.015 | 0.018 | 0.015 | 0.015 | 0.015 | 0.015 | — | — | 0.015 | 0.015 |
| Dye (ppm) | 40 | 40 | 40 | 40 | 40 | 40 | 11 | 30-300 | 30 | 30 |
| Ammonium Chloride | 0.100 | 0.118 | 0.100 | 0.100 | 0.115 | 0.115 | — | — | — | — |
| HCl | 0.012 | 0.014 | 0.012 | 0.012 | 0.028 | 0.028 | 0.016 | 0.025 | 0.011 | 0.011 |
| Structurant[l] | 0.01 | 0.01 | 0.01 | 0.01 | 0.01 | 0.01 | 0.01 | 0.01 | 0.01 | 0.01 |
| Additional Adjunct Perfume | 0.8 | 0.7 | 0.9 | 0.5 | 1.2 | 0.5 | 1.1 | 0.6 | 1.0 | 0.9 |
| Deionized Water | † | † | † | † | † | † | † | † | † | † |

[a]N,N-di(tallowoyloxyethyl)-N,N-dimethylammonium chloride.

[b]Methyl bis(tallow amidoethyl)2-hydroxyethyl ammonium methyl sulfate.

[c]Reaction product of Fatty acid with Methyldiethanolamine in a molar ratio 1.5:1, quaternized with Methylchloride, resulting in a 1:1 molar mixture of N,N-bis(stearoyl-oxy-ethyl) N,N-dimethyl ammonium chloride and N-(stearoyl-oxy-ethyl) N,-hydroxyethyl N,N dimethyl ammonium chloride.

[d]Cationic high amylose maize starch available from National Starch under the trade name CATO ®.

[e]Perfume from Example 1.

[f]Copolymer of ethylene oxide and terephthalate having the formula described in U.S. Pat. No. 5,574,179 at col. 15, lines 1-5, wherein each X is methyl, each n is 40, u is 4, each R1 is essentially 1,4-phenylene moieties, each R2 is essentially ethylene, 1,2-propylene moieties, or mixtures thereof.

[g]SE39 from Wacker

[h]Diethylenetriaminepentaacetic acid.

[i]KATHON ® CG available from Rohm and Haas Co. "PPM" is "parts per million."

[j]Gluteraldehyde

[k]Silicone antifoam agent available from Dow Corning Corp. under the trade name DC2310.

[l]Hydrophobically-modified ethoxylated urethane available from Rohm and Haas under the tradename Aculan 44.

* One or more materials comprising an amine moiety as disclosed in the present specification.

† balance

Example 6 Dry Laundry Formulations

| Component | % w/w granular laundry detergent composition | | | | | | |
|---|---|---|---|---|---|---|---|
| | A | B | C | D | E | F | G |
| Brightener | 0.1 | 0.1 | 0.1 | 0.2 | 0.1 | 0.2 | 0.1 |
| Soap | 0.6 | 0.6 | 0.6 | 0.6 | 0.6 | 0.6 | 0.6 |
| Ethylenediamine disuccinic acid | 0.1 | 0.1 | 0.1 | 0.1 | 0.1 | 0.1 | 0.1 |
| Acrylate/maleate copolymer | 1.5 | 1.5 | 1.5 | 1.5 | 1.5 | 1.5 | 1.5 |
| Hydroxyethane di(methylene phosphonic acid) | 0.4 | 0.4 | 0.4 | 0.4 | 0.4 | 0.4 | 0.4 |
| Mono-$C_{12-14}$ alkyl, di-methyl, mono-hydroyethyl quaternary ammonium chloride | 0.5 | 0.5 | 0.5 | 0.5 | 0.5 | 0.5 | 0.5 |
| Linear alkyl benzene | 0.1 | 0.1 | 0.2 | 0.1 | 0.1 | 0.2 | 0.1 |
| Linear alkyl benzene sulphonate | 10.3 | 10.1 | 19.9 | 14.7 | 10.3 | 17 | 10.5 |
| Magnesium sulphate | 0.4 | 0.4 | 0.4 | 0.4 | 0.4 | 0.4 | 0.4 |
| Sodium carbonate | 19.5 | 19.2 | 10.1 | 18.5 | 29.9 | 10.1 | 16.8 |
| Sodium sulphate | 29.6 | 29.8 | 38.8 | 15.1 | 24.4 | 19.7 | 19.1 |
| Sodium Chloride | 0.1 | 0.1 | 0.1 | 0.1 | 0.1 | 0.1 | 0.1 |
| Zeolite | 9.6 | 9.4 | 8.1 | 18 | 10 | 13.2 | 17.3 |
| Photobleach particle | 0.1 | 0.1 | 0.2 | 0.1 | 0.2 | 0.1 | 0.2 |

-continued

Example 6 Dry Laundry Formulations

| Component | A | B | C | D | E | F | G |
|---|---|---|---|---|---|---|---|
| | % w/w granular laundry detergent composition | | | | | | |
| Blue and red carbonate speckles | 1.8 | 1.8 | 1.8 | 1.8 | 1.8 | 1.8 | 1.8 |
| Ethoxylated Alcohol AE7 | 1 | 1 | 1 | 1 | 1 | 1 | 1 |
| Tetraacetyl ethylene diamine agglomerate (92 wt % active) | 0.9 | 0.9 | 0.9 | 0.9 | 0.9 | 0.9 | 0.9 |
| Citric acid | 1.4 | 1.4 | 1.4 | 1.4 | 1.4 | 1.4 | 1.4 |
| PDMS/clay agglomerates (9.5% wt % active PDMS) | 10.5 | 10.3 | 5 | 15 | 5.1 | 7.3 | 10.2 |
| Polyethylene oxide | 0.2 | 0.2 | 0.2 | 0.2 | 0.2 | 0.2 | 0.2 |
| Enzymes e.g. Protease (84 mg/g active), Amylase (22 mg/g active) | 0.2 | 0.3 | 0.2 | 0.1 | 0.2 | 0.1 | 0.2 |
| Suds suppressor agglomerate (12.4 wt % active) | 0.2 | 0.2 | 0.2 | 0.2 | 0.2 | 0.2 | 0.2 |
| Sodium percarbonate (having from 12% to 15% active AvOx) | 7.2 | 7.1 | 4.9 | 5.4 | 6.9 | 19.3 | 13.1 |
| Additional Adjunct Perfume** | 0.5 | 0.5 | 0.5 | 0.5 | 0.5 | 0.5 | 0.5 |
| Amine* | 0.1 | 0.5 | 0.0 | 0.01 | 0.02 | 0.00 | 0.07 |
| Perfume Delivery System As Disclosed In The Present Specification Including Examples 2-4 | 0.05 | 0.0 | 0.1 | 0.0 | 0.2 | 0.4 | 0.0 |
| Perfume comprising one or more PRMs from Example 1 | 0.3 | 0.4 | 0.01 | 0.02 | 0.04 | 0.1 | 0.1 |
| Water | 1.4 | 1.4 | 1.4 | 1.4 | 1.4 | 1.4 | 1.4 |
| Misc | 0.1 | 0.1 | 0.1 | 0.1 | 0.1 | 0.1 | 0.1 |
| Total Parts | 100 | 100 | 100 | 100 | 100 | 100 | 100 |

*One or more materials comprising an amine moiety as disclosed in the present specification.
**Optional Example 7 Liquid Laundry Formulations (HDLs)

| Ingredient | HDL 1 | HDL 2 | HDL3 | HDL4 | HDL 5 | HDL 6 |
|---|---|---|---|---|---|---|
| Alkyl Ether Sulphate | 0.00 | 0.50 | 12.0 | 12.0 | 6.0 | 7.0 |
| Dodecyl Benzene Sulphonic Acid | 8.0 | 8.0 | 1.0 | 1.0 | 2.0 | 3.0 |
| Ethoxylated Alcohol | 8.0 | 6.0 | 5.0 | 7.0 | 5.0 | 3.0 |
| Citric Acid | 5.0 | 3.0 | 3.0 | 5.0 | 2.0 | 3.0 |
| Fatty Acid | 3.0 | 5.0 | 5.0 | 3.0 | 6.0 | 5.0 |
| Ethoxysulfated hexamethylene diamine quaternized | 1.9 | 1.2 | 1.5 | 2.0 | 1.0 | 1.0 |
| Diethylene triamine penta methylene phosphonic acid | 0.3 | 0.2 | 0.2 | 0.3 | 0.1 | 0.2 |
| Enzymes | 1.20 | 0.80 | 0 | 1.2 | 0 | 0.8 |
| Brightener (disulphonated diamino stilbene based FWA) | 0.14 | 0.09 | 0 | 0.14 | 0.01 | 0.09 |
| Cationic hydroxyethyl cellulose | 0 | 0 | 0.10 | 0 | 0.200 | 0.30 |
| Poly(acrylamide-co-diallyldimethylammonium chloride) | 0 | 0 | 0 | 0.50 | 0.10 | 0 |
| Hydrogenated Castor Oil Structurant | 0.50 | 0.44 | 0.2 | 0.2 | 0.3 | 0.3 |
| Boric acid | 2.4 | 1.5 | 1.0 | 2.4 | 1.0 | 1.5 |
| Ethanol | 0.50 | 1.0 | 2.0 | 2.0 | 1.0 | 1.0 |
| 1,2 propanediol | 2.0 | 3.0 | 1.0 | 1.0 | 0.01 | 0.01 |
| Glutaraldehyde | 0 | 0 | 19 ppm | 0 | 13 ppm | 0 |
| Diethyleneglycol (DEG) | 1.6 | 0 | 0 | 0 | 0 | 0 |
| 2,3-Methyl-1,3-propanediol (M pdiol) | 1.0 | 1.0 | 0 | 0 | 0 | 0 |
| Mono Ethanol Amine | 1.0 | 0.5 | 0 | 0 | 0 | 0 |
| NaOH Sufficient To Provide Formulation pH of: | pH 8 | pH 8 | pH 8 | pH 8 | pH 8 | pH 8 |
| Sodium Cumene Sulphonate (NaCS) | 2.00 | 0 | 0 | 0 | 0 | 0 |
| Silicone (PDMS) emulsion | 0.003 | 0.003 | 0.003 | 0.003 | 0.003 | 0.003 |
| Additional Adjunct Perfume** | 0.7 | 0.5 | 0.8 | 0.6 | 0.6 | 0.5 |

-continued

| Example 7 Liquid Laundry Formulations (HDLs) | | | | | | |
|---|---|---|---|---|---|---|
| Ingredient | HDL 1 | HDL 2 | HDL3 | HDL4 | HDL 5 | HDL 6 |
| Amine* | 0.01 | 0.10 | 0.0 | 0.10 | 0.20 | 0.05 |
| Perfume from Example 1 | 0.02 | 0.15 | 0.10 | 0.2 | 0.3 | 0.05 |
| Perfume Delivery System As Disclosed In The Present Specification Including Examples 2-4 | 0.2 | 0.02 | 0.4 | 0.0 | 0.0 | 0.0 |
| Water | Balance | Balance | Balance | Balance | Balance | Balance |

*One or more materials comprising an amine moiety as disclosed in the present specification.

**Optional.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A perfume comprising zero weight percent p-tert.Butyl-alpha-methyldihydrocinnamic aldehyde and from about 0.01 to about 80 weight percent of a cocktail selected from:

a) a cocktail comprising, based on total cocktail weight, from about 0.01 to about 10 weight percent Octahydro-4,7-methanoindanilydenebutanal and from about 0.001 to about 5 weight percent 4,8-Dimethyldeca-4,9-dienal;

b) a cocktail comprising, based on total cocktail weight, from about 0.1 to about 50 weight percent Benzenepropanal, beta.-methyl-3-(1-methylethyl)-, and from about 0.1 to about 20 weight percent Isohexenyl cyclohexenyl carboxaldehyde;

c) a cocktail comprising, based on total cocktail weight, from about 0.1 to about 50 weight percent Benzenepropanal, .alpha.-methyl-4-(1-methylethyl)- and from about 10 to about 100 weight percent 2-(2-Methylpropyl)-4-methyl-tetrahydro-2H-pyran-4-ol;

d) a cocktail comprising, based on total cocktail weight, from about 0.001 to about 5 weight percent Acetaldehyde, [(3,7-dimethyl-6-octenyl)oxy]- and from about 0.1 to about 75 weight percent Benzenepropanal, .alpha.-methyl-4-(1-methylethyl)- and from about 25 to about 100 weight percent Octanal, 7-hydroxy-3,7-dimethyl-;

e) a cocktail comprising, based on total cocktail weight, from about 0.001 to about 5 weight percent Acetaldehyde, [(3,7-dimethyl-6-octenyl)oxy]- and from about 0.1 to about 75 weight percent Benzenepropanal, .alpha.-methyl-4-(1-methylethyl)- and from about 25 to about 100 weight percent Benzoic acid, 2-hydroxy-, hexyl ester;

f) a cocktail comprising, based on total cocktail weight, from about 10 to about 100 weight percent Benzoic acid, 2-hydroxy-, phenylmethyl ester, and from about 0.1 to about 50 weight percent 4-(1,1-Dimethylethyl)benzenepropanal and from about 0.1 to about 50 weight percent Octahydro-8,8-dimethylnaphthalene-2-carboxaldehyde and from about 0.1 to about 75 weight percent Benzenepropanal, alpha.-methyl-4-(1-methylethyl)-, and from about 1 to about 75 weight percent Benzoic acid, 2-hydroxy-, hexyl ester and from about 0.1 to about 75 weight percent 1,6-Octadien-3-ol, 3,7-dimethyl-, and from about 0.1 to about 75 weight percent 3-Cyclohexene-1-carboxaldehyde, 4-(4-hydroxy-4-methylpentyl)-, and from about 0.1 to about 20 weight percent 2,6-Dimethyl-5-heptenal, and from about 0.1 to about 75 weight percent 2-Cyclohexylidene-2-phenylacetonitrile, and from about 0.1 to about 10 weight percent 3-hydroxy-2-butanone;

g) a cocktail comprising, based on total cocktail weight, from about 1 to about 75 weight percent n-Pentyl salicylate and from about 1 to about 75 weight percent Benzoic acid, 2-hydroxy-, phenylmethyl ester and from about 0.1 to about 25 weight percent Benzoic acid, 2-hydroxy-, 3-hexenyl ester, (Z)—, and from about 1 to about 75 weight percent Benzoic acid, 2-hydroxy-, cyclohexyl ester and from about 0.1 to about 20 weight percent Octahydro-4,7-methanoindanilydenebutanal, and from about 0.1 to about 20 weight percent 4,8-Dimethyldeca-4,9-dienal and from about 1 to about 75 weight percent Benzoic acid, 2-hydroxy-, hexyl ester and from about 1 to about 75 weight percent Hexahydro-4,7-methanoinden5(6)yl isobutyrate;

h) a cocktail comprising, based on total cocktail weight, from about 1 to about 75 weight percent n-Pentyl salicylate and from about 1 to about 75 weight percent Benzoic acid, 2-hydroxy-, phenylmethyl ester and from about 1 to about 50 weight percent Benzoic acid, 2-hydroxy-, 3-hexenyl ester, (Z)—, and from about 1 to about 75 weight percent Benzoic acid, 2-hydroxy-, cyclohexyl ester, and from about 0.1 to about 25 weight percent Octahydro-8,8-dimethylnaphthalene-2-carboxaldehyde and from about 0.1 to about 20 weight percent Octahydro-4,7-methanoindanilydenebutanal and from about 0.1 to about 20 weight percent 4,8-Dimethyldeca-4,9-dienal and from about 1 to about 75 weight percent Benzoic acid, 2-hydroxy-, hexyl ester and from about 1 to about 75 weight percent 1,6-Octadien-3-ol, 3,7-dimethyl-, and from about 0.1 to about 50 weight percent Cyclohexanemethanol, 4-(1-methylethyl)-, cis-, and from about 0.1 to about 20 weight percent 2,6-Dimethyl-5-heptenal, and from about 0.1 to about 50 weight percent 2-Cyclohexylidene-2-phenylacetonitrile, and from about 0.1 to about 80 weight percent alpha-Hexylcinnamaldehyde, and from about 0.1 to about 50 weight percent Hexahydro-4,7-methanoinden5(6)yl isobutyrate, and from about 1 to about 75 weight percent 1,4-Dioxacycloheptadecane-5,17-dione, and from about 0.1 to about 5 weight percent Benzaldehyde, 4-hydroxy-3-methoxy-;

i) a cocktail comprising, based on total cocktail weight, from about 1 to about 75 weight percent Cyclohexanemethanol, 4-(1-methylethyl)-, cis-, and from about 1 to about 75 weight percent 2-Naphthaldehyde, 1,2,3,4,5,6,7,8-octahydro-8,8-dimethyl- (mixture), and from about 5 to about 90 weight percent 2-Octanol, 2,6-dimethyl-, and from about 1 to about 75 weight percent Methyl 2-hexyl-3-oxo-cyclopentanecarboxylate;

j) a cocktail comprising, based on total cocktail weight, from about 0.1 to about 50 weight percent 4-(1,1-Dimethylethyl)benzenepropanal and from about 0.1 to about 20 weight percent Octahydro-8,8-dimethylnaphthalene-2-carboxaldehyde and from about 1 to about 75 weight percent Benzenepropanal, .alpha.-methyl-4-(1-methylethyl)-, and from about 0.1 to about 20 weight percent Benzenepropanal, .beta.-methyl-3-(1-methylethyl)-, and from about 1 to about 75 weight percent Benzoic acid, 2-hydroxy-, hexyl ester, and from about 1 to about 75 weight percent 3-Cyclohexene-1-carboxaldehyde, 4-(4-hydroxy-4-methylpentyl)-, and from about 0.1 to about 20 weight percent 2,6-Dimethyl-5-heptenal, and from about 1 to about 75 weight percent Cyclopentaneacetic acid, 2-oxo-2 Phenyl-, methyl ester, and from about 1 to about 75 weight percent Hexahydro-4,7-methanoinden5(6)yl isobutyrate, and from about 1 to about 75 weight percent 3-Acetyl-3,4,10,10-tetramethylbicyclo[4.4.0]decane, and from about 0.01 to about 7.5 weight percent Dodecanal, and from about 0.1 to about 50 weight percent 2-(2(4-Methyl-3-cyclohexen-1-yl)propyl)-cyclopentanone, and from about 0.001 to about 5 weight percent 4-(4-Hydroxyphenyl)butanone-2;

k) a cocktail comprising, based on total cocktail weight, from about 0.1 to about 50 weight percent Benzoic acid, 2-[(7-hydroxy-3,7-dimethyloctylidene)amino]-, methyl, and from about 1 to about 75 weight percent 1,6-Octadien-3-ol, 3,7-dimethyl-, and from about 0.1 to about 25 weight percent Cyclohexanemethanol, 4-(1-methylethyl)-, cis-, and from about 0.01 to about 20 weight percent 2,6-Dimethyl-5-heptenal, and from about 0.01 to about 20 weight percent 2,6,10-Trimethyl-9-undecenal, and from about 0.1 to about 25 weight percent gamma-Decalactone, and from about 1 to about 90 weight percent Isohexenyl cyclohexenyl carboxaldehyde;

l) a cocktail comprising, based on total cocktail weight, from about 0.1 to about 50 weight percent 4-(1,1-Dimethylethyl)benzenepropanal, and from about 0.1 to about 75 weight percent Benzenepropanal, .alpha.-methyl-4-(1-methylethyl)-, and from about 10 to about 95 weight percent 3-(4-Isobutyl-phenyl)-2-methyl-propionaldehyde m) and mixtures thereof;

wherein a neat product odor of the cocktail is substantially the same as a neat product odor of p-tert.Butyl-alpha-methyldihydrocinnamic aldehyde.

2. A consumer product comprising, based on total consumer product weight, from about 0.0001% to about 100% of a perfume according to claim 1 and an adjunct ingredient, and optionally a perfume delivery system comprising a perfume raw material selected from the group consisting of n-Pentyl salicylate; Methyl-N-(7-hydroxy-3,7-dimethyloctylidene) anthranilate; Benzoic acid, 2-hydroxy-, phenylmethyl ester; 4-(1,1-Dimethylethyl)benzenepropanal; Benzoic acid, 2-hydroxy-, 3-hexenyl ester, (Z)—; Acetaldehyde, [(3,7-dimethyl-6-octenyl)oxy]-; Propanal, 3-(4-isopropylphenyl)-; Benzoic acid, 2-hydroxy-, cyclohexyl ester; Octahydro-8,8-dimethylnaphthalene-2-carboxaldehyde; dl-3,7-Dimethyl-6-octen-1-ol; trans-3,7-Dimethyl-2,6-octadien-1-ol; Cyclopentan-1-ol, 2 Pentyl; Benzenepropanal, .alpha.-methyl-4-(1-methylethyl)-; Octahydro-4,7-methanoindanilydenebutanal; 1,6-Nonadien-3-ol, 3,7-dimethyl-; 4,8-Dimethyldeca-4,9-dienal; Benzenepropanal, .beta.-methyl-3-(1-methylethyl)-; 2-(2-Methylpropyl)-4-methyl-tetrahydro-2H-pyran-4-ol; 2-Butyl-4,6-dimethyldihydropyran (isomers); Benzoic acid, 2-hydroxy-, hexyl ester; 2-Methyl-3-(3,4-methylenedioxyphenyl)-propanal; Octanal, 7-hydroxy-3,7-dimethyl-; 1,6-Octadien-3-ol, 3,7-dimethyl-; 3-Cyclohexene-1-carboxaldehyde, 4-(4-hydroxy-4-methylpentyl)-; 2,2-Dimethyl-3-(3-methylphenyl)-propanol; Cyclohexanemethanol, 4-(1-methylethyl)-, cis-; 2-Naphthaldehyde, 1,2,3,4,5,6,7,8-octahydro-8,8-dimethyl-(mixture); 2,6-Dimethyl-5-heptenal; 1-(4-Isopropylcyclohexyl)ethanol; 3-methyl-4-phenylbutan-2-ol; Dimethyl phenyl Propanol; 1H-Indene-ar-propanal. 2,3-dihydro-1,1-dimethyl-; Lilial/methyl anthranilate Schiff base; 2-Cyclohexylidene-2-phenylacetonitrile; 3-Methyl-5-phenyl-1-pentanol; 1-methyl-3-(2-methylpropyl)cyclohexan-1-ol; 2-Methyl-3-(4-(2-methylpropyl)phenyl)propanal; 3-(4-Isobutyl-phenyl)-2-methyl-propionaldehyde; 2-Octanol, 2,6-dimethyl-; 3,7-Dimethyloctanol-3; 2-[(4-methylphenyl) methylene]-heptanal; Methyl 2-hexyl-3-oxo-cyclopentanecarboxylate; alpha-Hexylcinnamaldehyde; Cyclopentaneacetic acid, 2-oxo-2 Phenyl-, methyl ester; (3-hydroxy-2-butanone); 2,6,10-Trimethyl-9-undecenal; 2-H 1,5-Benzodioxepin-3(4H)-one, 7 propyl-; 4H-4A, 9 Methanoazuleno (5,6 d)-1,3-dioxole, octahydro 2,2,5,8,8,9a-hexamethyl-; 3a,6,6,9a-Tetramethyl-dodecahydronaphtho[2,1-b]furan; 7(3-methyl butyl)-1,5-Benzodioxepin-3-one; 2-Ethyl-4-(2,2,3-trimethylcyclopent-3-enyl-1)-2-buten-1-ol; 3,4-Dioxy(cycloacetonyl)toluene; 3a,6,6,9a-Tetramethyl-dodecahydronaphtho[2,1-b]furan; 2-Propenol-1,3-phenyl-; 3,7-Dimethyl-2,6-octadienal; Hexahydro-4,7-methanoinden5(6)yl isobutyrate; Hexahydro-4,7-methanoinden-5(6)-yl acetate; Hexahydro-4,7-methanoinden-5(6)-yl propionate; Cyclohexadecanolide; 8-Cyclohexadecen-1-one; Cyclopentadecanone; 4-(2,6,6-Trimethyl-3-cyclohexen-1-yl)-but-3-en-4-one; 3-Methyl-5-(2,2,3-trimethyl-3-cyclopenten-1-yl)-4-penten-2-ol (& isomers); 1,6-Octadiene, 3-(1-ethoxyethoxy)-3,7-dimethyl-; Benzaldehyde, 3-ethoxy-4-hydroxy-; 1,4-Dioxacycloheptadecane-5,17-dione; 4-Cyclopentadecen-1-one, (Z)—; Oxacyclohexadecan-2-one; alpha,alpha-Dimethyl-p-ethylphenylpropanal; 1,4, Cyclohexanedicarboxylic acid, diethyl ester; gamma-Decalactone; Oxacyclohexadecen-2-one; 1-Propanol, 2-[1-(3,3-dimethyl-cyclohexyl)ethoxy]-2-methyl-propanoate; 1,3,4,6,7,8-Hexahydro-4,6,6,7,8,8-hexamethyl-cyclopenta-(g)-2-benzopyran; Cyclododecaneethanol, .beta.-methyl-; 3-Acetyl-3,4,10,10-tetramethylbicyclo[4.4.0]decane; Isohexenyl cyclohexenyl carboxaldehyde; 4-Acetoxy-3-pentyl-2H-tetrahydropyran and isomers; (1-Methyl-2-(1,2,2-trimethylbicyclo[3.1.0]-hex-3-ylmethyl)cyclopropyl)methanol (Mixture of diastereoisomers); Dodecanal; gamma-Methyl benzenepentanal; 5-Cyclopentadecen-1-one, 3 Methyl; 7-Acetyl-1,1,3,4,4,6-hexamethyltetralin; 2-(2(4-Methyl-3-cyclohexen-1-yl)propyl)-cyclopentanone; 1-(2,2,6-Trimethylcyclohexyl)hexanol-3; 1-(1,1-dimethylpropyl)-4-ethoxy-cyclohexane (mixture of cis & trans isomers); 4-(4-Hydroxyphenyl)butanone-2; 2-Norpinene-2-Propionaldehyde,6,6-Dimethyl; Acetic Acid, (1-oxopropoxy)-1-(3,3-dimethylcyclohexyl)ethyl ester; 2-ethyl-4-(2,2,3-trimethyl-3-cyclopenten-1-yl)-2-buten-1-ol; Cyclohexadecanolide and Cyclopentadecanone mixture; Terpineol (alpha,beta,gamma); Benzaldehyde, 4-hydroxy-3-methoxy-; and 5-Cyclohexadecenone-1.

3. A cleaning and/or treatment composition comprising based on total cleaning and treatment products weight from about 0.0001% to about 25% of a perfume according to claim 1 and an adjunct ingredient.

4. A fabric and/or hard surface cleaning and/or treatment composition comprising, based on total fabric and/or hard surface cleaning and/or treatment composition weight of from about 0.00001% to about 25% of a perfume according to claim 1 and an adjunct ingredient.

5. A detergent comprising, based on total fabric and/or hard surface cleaning and/or treatment composition weight of from about 0.00001% to about 25% of a perfume according to claim 1 and an adjunct ingredient.

6. A highly compacted consumer product comprising, based on total highly compacted consumer product composition weight, from about 0.00001% to about 25% of a perfume according to claim 1 and an adjunct ingredient.

7. A consumer product according to claim 2 comprising, based on total consumer product weight, from about 0.001% to about 20% of a perfume raw material selected from the group consisting of n-Pentyl salicylate; Methyl-N-(7-hydroxy-3,7-dimethyloctylidene)anthranilate; Benzoic acid, 2-hydroxy-, phenylmethyl ester; 4-(1,1-Dimethylethyl)benzenepropanal; Benzoic acid, 2-hydroxy-, 3-hexenyl ester, (Z)—; Acetaldehyde, [(3,7-dimethyl-6-octenyl)oxy]-; Propanal, 3-(4-isopropylphenyl)-; Benzoic acid, 2-hydroxy-, cyclohexyl ester; Octahydro-8,8-dimethylnaphthalene-2-carboxaldehyde; dl-3,7-Dimethyl-6-octen-1-ol; trans-3,7-Dimethyl-2,6-octadien-1-ol; Cyclopentan-1-ol, 2 Pentyl; Benzenepropanal, .alpha.-methyl-4-(1-methylethyl)-; Octahydro-4,7-methanoindanilydenebutanal; 1,6-Nonadien-3-ol, 3,7-dimethyl-; 4,8-Dimethyldeca-4,9-dienal; Benzenepropanal, .beta.-methyl-3-(1-methylethyl)-; 2-(2-Methylpropyl)-4-methyl-tetrahydro-2H-pyran-4-ol; 2-Butyl-4,6-dimethyldihydropyran (isomers); Benzoic acid, 2-hydroxy-, hexyl ester; 2-Methyl-3-(3,4-methylenedioxyphenyl)-propanal; Octanal, 7-hydroxy-3,7-dimethyl-; 1,6-Octadien-3-ol, 3,7-dimethyl-; 3-Cyclohexene-1-carboxaldehyde, 4-(4-hydroxy-4-methylpentyl)-; 2,2-Dimethyl-3-(3-methylphenyl)-propanol; Cyclohexanemethanol, 4-(1-methylethyl)-, cis-; 2-Naphthaldehyde, 1,2,3,4,5,6,7,8-octahydro-8,8-dimethyl-(mixture); 2,6-Dimethyl-5-heptenal; 1-(4-Isopropylcyclohexyl)ethanol; 3-methyl-4-phenylbutan-2-ol; Dimethyl phenyl Propanol; 1H-Indene-ar-propanal. 2,3-dihydro-1,1-dimethyl-; Lilial/methyl anthranilate Schiff base; 2-Cyclohexylidene-2-phenylacetonitrile; 3-Methyl-5-phenyl-1-pentanol; 1-methyl-3-(2-methylpropyl)cyclohexan-1-ol; 2-Methyl-3-(4-(2-methylpropyl)phenyl)propanal; 3-(4-Isobutyl-phenyl)-2-methyl-propionaldehyde; 2-Octanol, 2,6-dimethyl-; 3,7-Dimethyloctanol-3; 2-[(4-methylphenyl)methylene]-heptanal; Methyl 2-hexyl-3-oxo-cyclopentanecarboxylate; alpha-Hexylcinnamaldehyde; Cyclopentaneacetic acid, 2-oxo-2 Phenyl-, methyl ester; (3-hydroxy-2-butanone); 2,6,10-Trimethyl-9-undecenal; 2-H 1,5-Benzodioxepin-3(4H)-one, 7 propyl-; 4H-4A, 9 Methanoazuleno (5,6 d)-1,3-dioxole, octahydro 2,2,5,8,8,9a-hexamethyl-; 3a,6,6,9a-Tetramethyl-dodecahydronaphtho[2,1-b]furan; 7(3-methyl butyl)-1,5-Benzodioxepin-3-one; 2-Ethyl-4-(2,2,3-trimethylcyclopent-3-enyl-1)-2-buten-1-ol; 3,4-Dioxy(cycloacetonyl)toluene; 3a,6,6,9a-Tetramethyl-dodecahydronaphtho[2,1-b]furan; 2-Propenol-1,3-phenyl-; 3,7-Dimethyl-2,6-octadienal; Hexahydro-4,7-methanoinden5(6)yl isobutyrate; Hexahydro-4,7-methanoinden-5(6)-yl acetate; Hexahydro-4,7-methanoinden-5(6)-yl propionate; Cyclohexadecanolide; 8-Cyclohexadecen-1-one; Cyclopentadecanone; 4-(2,6,6-Trimethyl-3-cyclohexen-1-yl)-but-3-en-4-one; 3-Methyl-5-(2,2,3-trimethyl-3-cyclopenten-1-yl)-4-penten-2-ol (& isomers); 1,6-Octadiene, 3-(1-ethoxyethoxy)-3,7-dimethyl-; Benzaldehyde, 3-ethoxy-4-hydroxy-; 1,4-Dioxacycloheptadecane-5,17-dione; 4-Cyclopentadecen-1-one, (Z)—; Oxacyclohexadecan-2-one; alpha,alpha-Dimethyl-p-ethylphenylpropanal; 1,4, Cyclohexanedicarboxylic acid, diethyl ester; gamma-Decalactone; Oxacyclohexadecen-2-one; 1-Propanol, 2-[1-(3,3-dimethyl-cyclohexyl)ethoxy]-2-methyl-propanoate; 1,3,4,6,7,8-Hexahydro-4,6,6,7,8,8-hexamethyl-cyclopenta-(g)-2-benzopyran; Cyclododecaneethanol, .beta.-methyl-; 3-Acetyl-3,4,10,10-tetramethylbicyclo[4.4.0]decane; Isohexenyl cyclohexenyl carboxaldehyde; 4-Acetoxy-3-pentyl-2H-tetrahydropyran and isomers; (1-Methyl-2-(1,2,2-trimethylbicyclo[3.1.0]-hex-3-ylmethyl)cyclopropyl)methanol (Mixture of diastereoisomers); Dodecanal; gamma-Methyl benzenepentanal; 5-Cyclopentadecen-1-one, 3 Methyl; 7-Acetyl-1,1,3,4,4,6-hexamethyltetralin; 2-(2(4-Methyl-3-cyclohexen-1-yl)propyl)-cyclopentanone; 1-(2,2,6-Trimethylcyclohexyl)hexanol-3; 1-(1,1-dimethylpropyl)-4-ethoxy-cyclohexane (mixture of cis & trans isomers); 4-(4-Hydroxyphenyl)butanone-2; 2-Norpinene-2-Propionaldehyde,6,6-Dimethyl; Acetic Acid, (1-oxopropoxy)-1-(3,3-dimethylcyclohexyl)ethyl ester; 2-ethyl-4-(2,2,3-trimethyl-3-cyclopenten-1-yl)-2-buten-1-ol; Cyclohexadecanolide and Cyclopentadecanone mixture; Terpineol (alpha,beta,gamma); Benzaldehyde, 4-hydroxy-3-methoxy-; and 5-Cyclohexadecenone-1 and/or a stereoisomers thereof and an adjunct ingredient.

8. A method of cleaning or treating a situs comprising optionally washing and/or rinsing said situs, contacting said situs with the composition selected from the compositions of claims 1-7 and mixtures thereof and optionally washing and/or rinsing said situs.

* * * * *